US009899700B2

(12) United States Patent
Otts et al.

(10) Patent No.: US 9,899,700 B2
(45) Date of Patent: Feb. 20, 2018

(54) METHODS TO FORM BIOCOMPATIBLE ENERGIZATION ELEMENTS FOR BIOMEDICAL DEVICES COMPRISING LAMINATES AND DEPOSITED SEPARATORS

(71) Applicant: Johnson & Johnson Vision Care, Inc., Jacksonville, FL (US)

(72) Inventors: Daniel B. Otts, Fruit Cove, FL (US); Randall B. Pugh, St. Johns, FL (US); James Daniel Riall, St. Johns, FL (US); Adam Toner, Jacksonville, FL (US); Frederick A. Flitsch, New Windsor, NY (US); Shivkumar Mahadevan, Orange Park, FL (US)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 372 days.

(21) Appl. No.: 14/687,351

(22) Filed: Apr. 15, 2015

(65) Prior Publication Data
US 2016/0056494 A1   Feb. 25, 2016

Related U.S. Application Data

(60) Provisional application No. 62/040,178, filed on Aug. 21, 2014.

(51) Int. Cl.
*H01M 10/04*     (2006.01)
*B29D 11/00*     (2006.01)
(Continued)

(52) U.S. Cl.
CPC ..... *H01M 10/049* (2013.01); *B29D 11/00817* (2013.01); *H01M 2/026* (2013.01);
(Continued)

(58) Field of Classification Search
None
See application file for complete search history.

(56) References Cited

U.S. PATENT DOCUMENTS 3,642,539 A   2/1972   Kawakami
4,125,686 A   11/1978  Kinsman
(Continued)

FOREIGN PATENT DOCUMENTS

CA   2389907 A1   12/2003
CN   102959769 A    3/2013
(Continued)

OTHER PUBLICATIONS

Elena A. Belyaeva et al., "Mechanism(s) of Toxic Action of Zn2+ and Selenite: A Study on AS-30D Hepatoma Cells and Isolated Mitochondria", Biochemistry Research International, vol. 42, No. 6, Jan. 1, 2011, pp. 361-413.
(Continued)

*Primary Examiner* — Barbara L Gilliam
*Assistant Examiner* — Wyatt P McConnell

(57) ABSTRACT

Methods and apparatus to form biocompatible energization elements are described. In some examples, the methods and apparatus to form the biocompatible energization elements involve forming cavities comprising active cathode chemistry and depositing separators within a laminate structure of the battery. The active elements of the cathode and anode are sealed with a laminate stack of biocompatible material. In some examples, a field of use for the methods and apparatus may include any biocompatible device or product that requires energization elements.

30 Claims, 14 Drawing Sheets

(51) Int. Cl.

| | | |
|---|---|---|
| *H01M 6/40* | (2006.01) | |
| *H01M 4/50* | (2010.01) | |
| *H01M 6/12* | (2006.01) | |
| *H01M 2/02* | (2006.01) | |
| A61B 17/00 | (2006.01) | |
| H01M 6/32 | (2006.01) | |
| H01M 6/42 | (2006.01) | |
| B29L 11/00 | (2006.01) | |

(52) U.S. Cl.
CPC ............. *H01M 4/50* (2013.01); *H01M 6/12* (2013.01); *H01M 6/40* (2013.01); *A61B 2017/00734* (2013.01); *A61B 2560/0214* (2013.01); *A61M 2205/04* (2013.01); *A61M 2205/8206* (2013.01); *B29L 2011/0041* (2013.01); *H01M 6/32* (2013.01); *H01M 6/425* (2013.01); *H01M 2220/30* (2013.01)

(56) References Cited

U.S. PATENT DOCUMENTS

| | | | |
|---|---|---|---|
| 4,977,046 | A | 12/1990 | Bleszinski, Jr. |
| 5,358,539 | A | 10/1994 | Dawson |
| 5,540,741 | A | 7/1996 | Gozdz et al. |
| 5,607,485 | A | 3/1997 | Gozdz et al. |
| 5,712,721 | A | 1/1998 | Large |
| 6,273,904 | B1 | 8/2001 | Chen |
| 6,277,520 | B1 | 8/2001 | Moutsios |
| 6,316,142 | B1 | 11/2001 | Delnick |
| 6,379,835 | B1 | 4/2002 | Kucherovsky |
| 2002/0041999 | A1* | 4/2002 | Moutsios ............ H01M 2/0212 429/224 |
| 2002/0110728 | A1 | 8/2002 | Gozdz et al. |
| 2003/0146414 | A1 | 8/2003 | Ndzebet |
| 2003/0207978 | A1 | 11/2003 | Yadav |
| 2004/0062985 | A1 | 4/2004 | Aamodt |
| 2004/0091779 | A1 | 5/2004 | Kang |
| 2004/0258982 | A1 | 12/2004 | Coffey |
| 2005/0208381 | A1 | 9/2005 | Boulton |
| 2006/0099496 | A1 | 5/2006 | Aamodt |
| 2007/0125644 | A1 | 6/2007 | Heller |
| 2007/0141463 | A1 | 6/2007 | Stevanovic |
| 2007/0156184 | A1 | 7/2007 | Root |
| 2009/0092903 | A1 | 4/2009 | Johnson |
| 2009/0098281 | A1 | 4/2009 | Zhang |
| 2010/0072643 | A1 | 3/2010 | Pugh |
| 2010/0078837 | A1 | 4/2010 | Pugh |
| 2010/0266895 | A1 | 10/2010 | Tucholski |
| 2011/0091778 | A1 | 4/2011 | Kambara |
| 2012/0107666 | A1 | 5/2012 | Bailey |
| 2012/0115041 | A1 | 5/2012 | West |
| 2012/0162600 | A1 | 6/2012 | Pugh |
| 2013/0089769 | A1 | 4/2013 | Proctor |
| 2013/0155371 | A1 | 6/2013 | Zhang |
| 2013/0196214 | A1 | 8/2013 | Scott |
| 2013/0309547 | A1 | 11/2013 | Bazzarella |
| 2014/0000101 | A1 | 1/2014 | Pugh |
| 2014/0121557 | A1 | 5/2014 | Gannon |
| 2014/0147742 | A1 | 5/2014 | Anastas |
| 2015/0214567 | A1 | 7/2015 | Etzkorn |
| 2015/0287960 | A1 | 10/2015 | Andry |

FOREIGN PATENT DOCUMENTS

| | | |
|---|---|---|
| EP | 918248 A2 | 5/1999 |
| EP | 1183745 A1 | 3/2002 |
| EP | 1313159 A2 | 5/2003 |
| EP | 1892788 A1 | 2/2008 |
| EP | 2564454 A1 | 3/2013 |
| EP | 2779272 A1 | 9/2014 |
| GB | 1307393 A | 2/1973 |
| IL | 222620D0 | 12/2012 |
| WO | WO1997017737 A1 | 5/1997 |
| WO | WO2000004601 A1 | 1/2000 |
| WO | WO2000057504 A1 | 9/2000 |
| WO | WO2002029836 A1 | 4/2002 |
| WO | WO2005064712 A1 | 7/2005 |
| WO | WO2009012463 A2 | 1/2009 |
| WO | WO2009018315 A2 | 2/2009 |
| WO | WO2011015866 A1 | 2/2011 |
| WO | WO2011137239 A1 | 11/2011 |
| WO | WO2012046854 A1 | 4/2012 |
| WO | WO2013128206 A1 | 9/2013 |
| WO | WO2014071571 A1 | 5/2014 |

OTHER PUBLICATIONS

Albano et al., "Design of an Implantable power supply for an intraocular sensor, using POWER (power optimization for wireless energy requirements)" Journal of Power Soureces, Elsevier SA, CH, vol. 170, No. 1, Apr. 11, 2007, pp. 216-224.

Stani A. et al., "Development of flat plate rechargeable alkaline manganese dioxide-zinc cells", Journal of Power Sources, Elsevier SA, vol. 153, No. 2, Jun. 28, 2005, pp. 405-412.

Geduld, Herb, "Zinc Plating", XP055290076, Columbia Chemical Corp., Macedonia, OH Jan. 1, 1988.

Fernando Yanez et al., "Macromolecule release and smoothness of semi-interpenetrating PVP-pHEMA networks for comfortable soft contact lenses", European Journal of Pharmaceutics, Elsevier Science Publishers B.V., Amsterdam, NL, vol. 69, No. 3, Aug. 1, 2008, pp. 1094-1103, XP023519572, ISSN: 0939-6411.

* cited by examiner

FIG. 1A
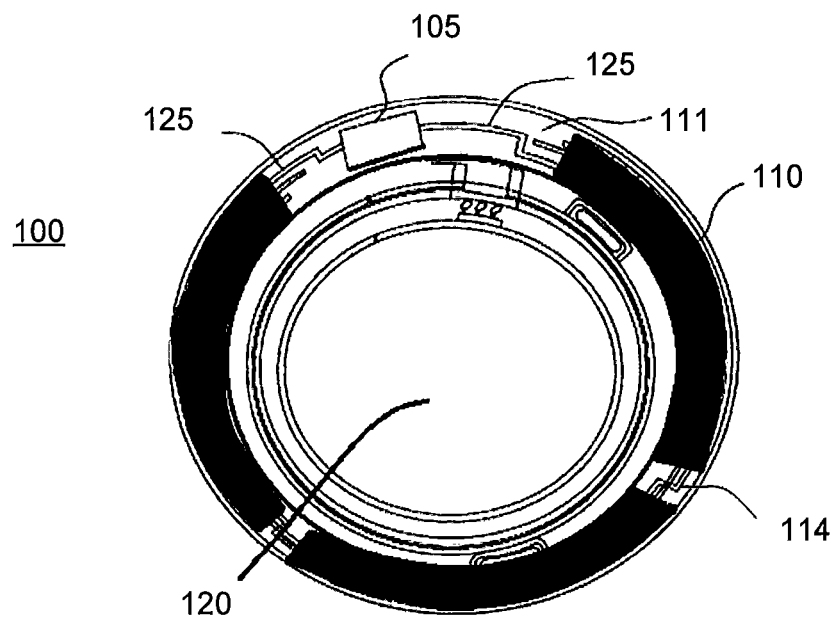
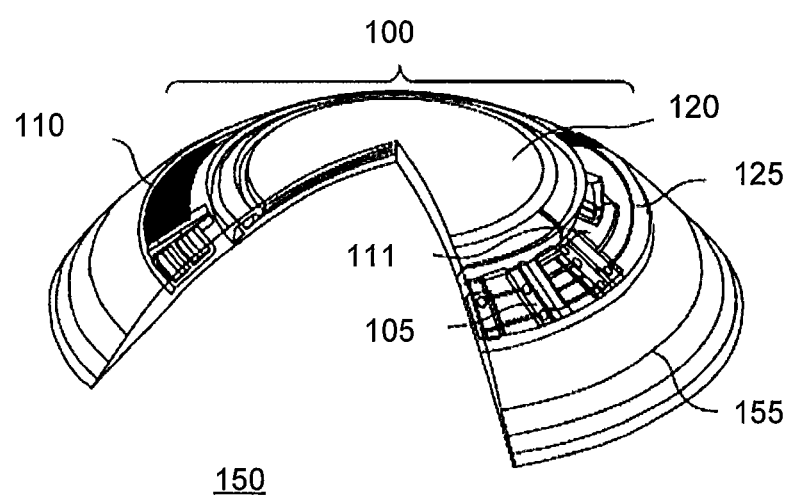
FIG. 1B

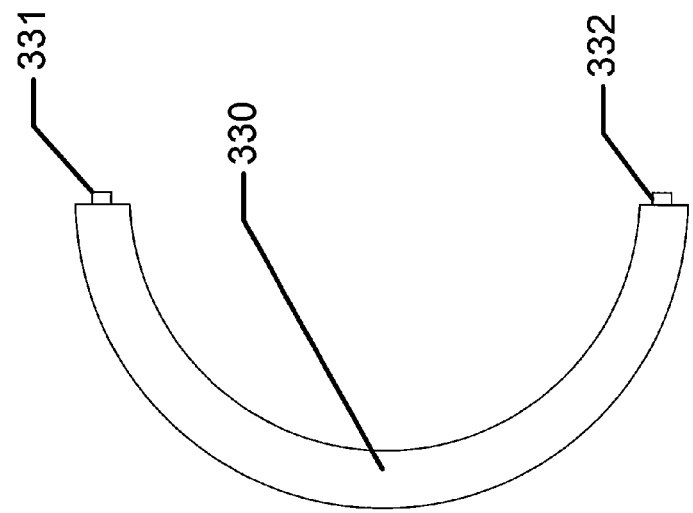
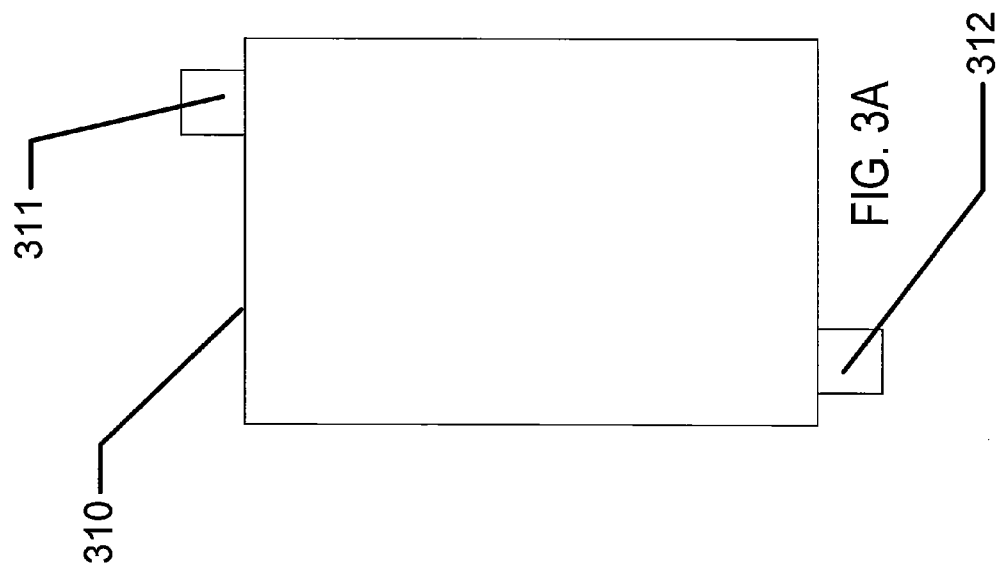

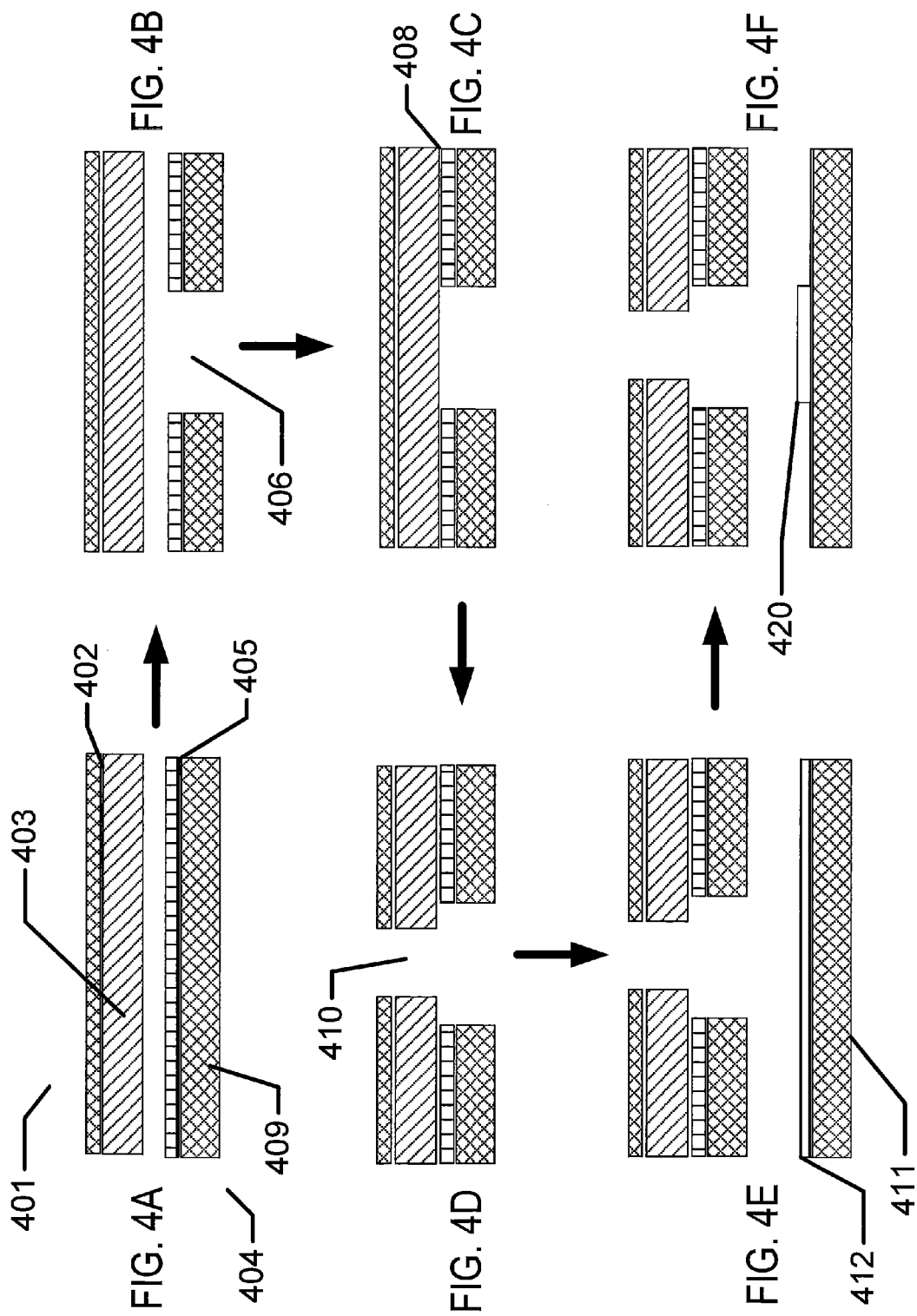

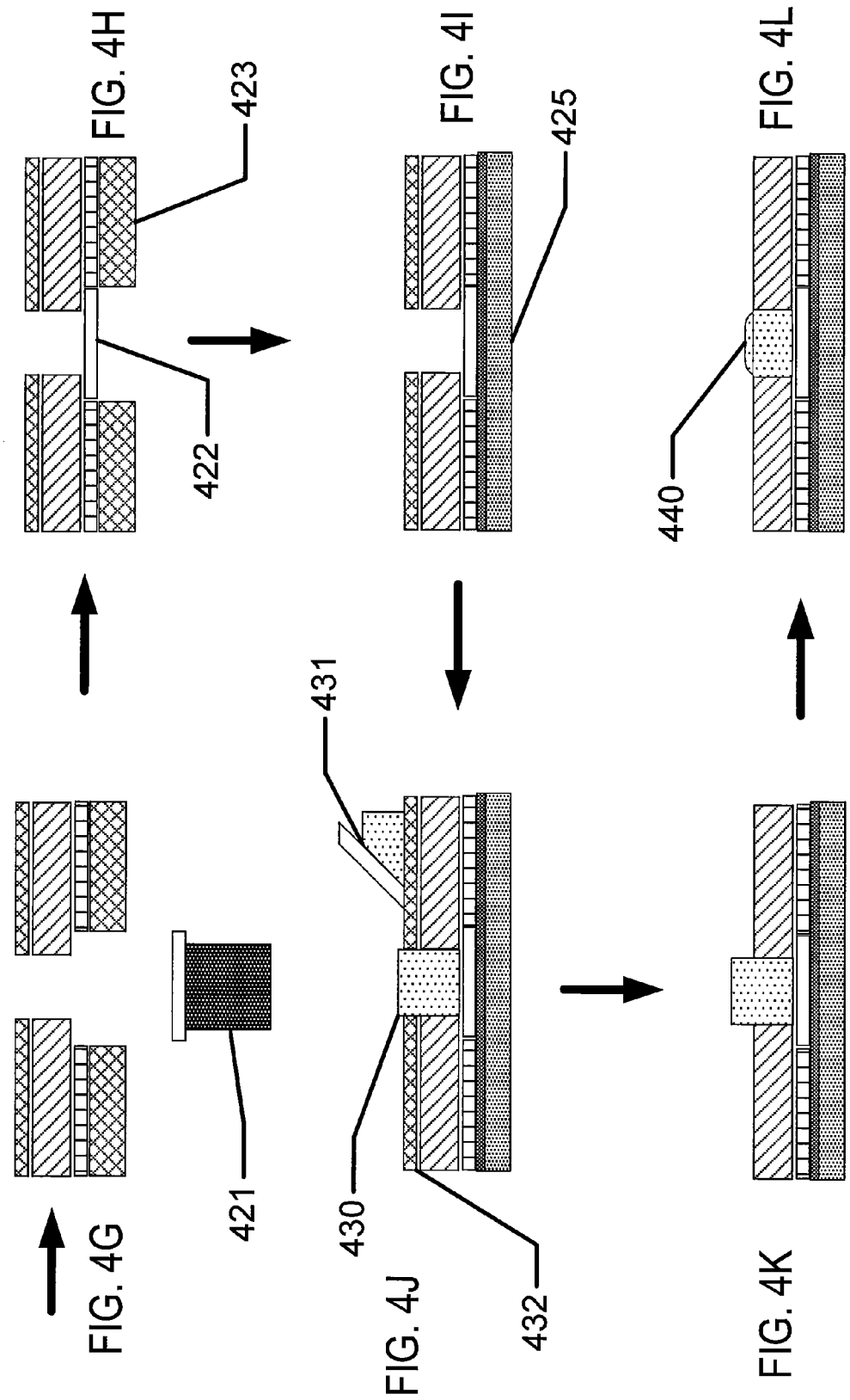

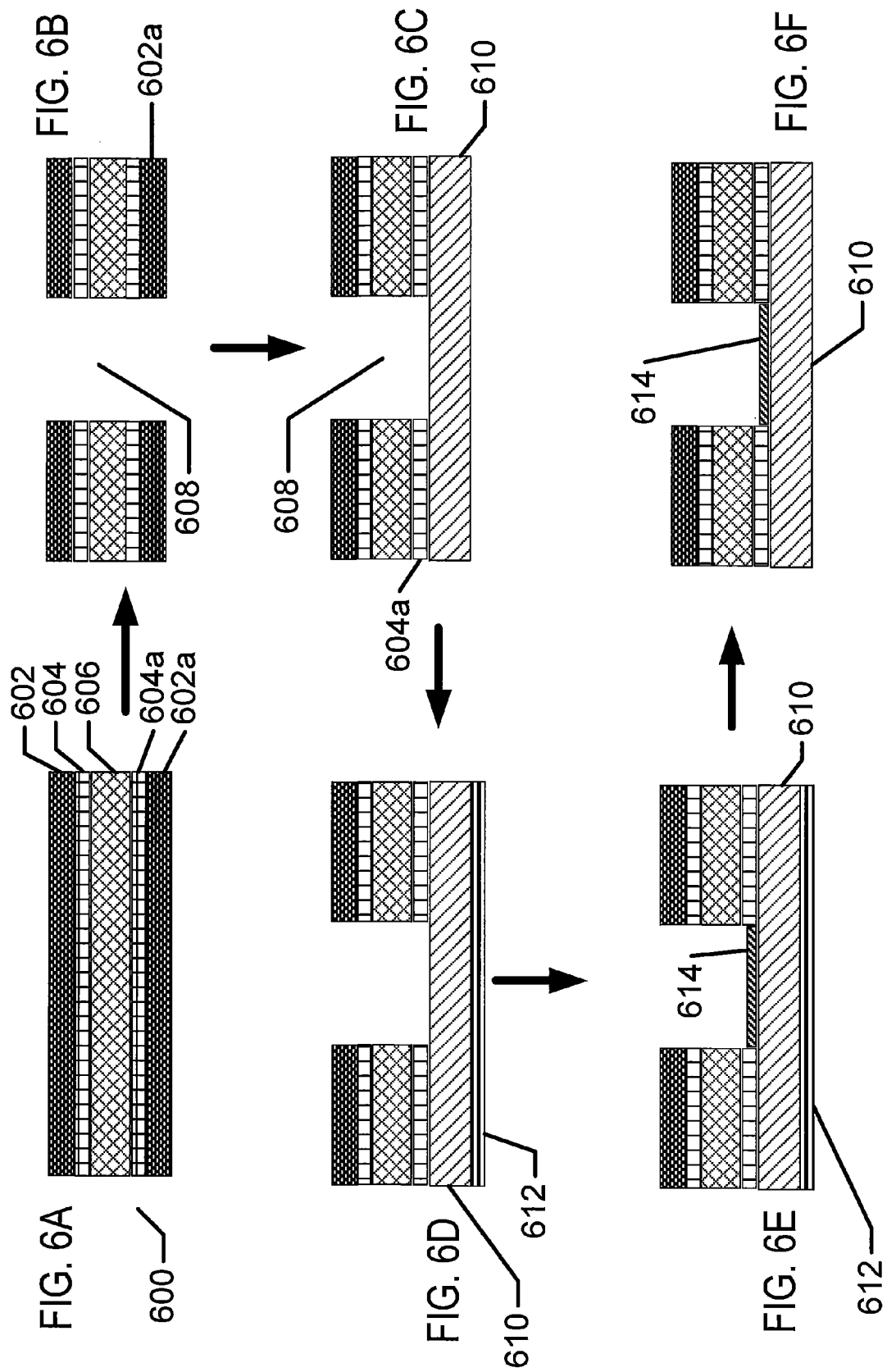

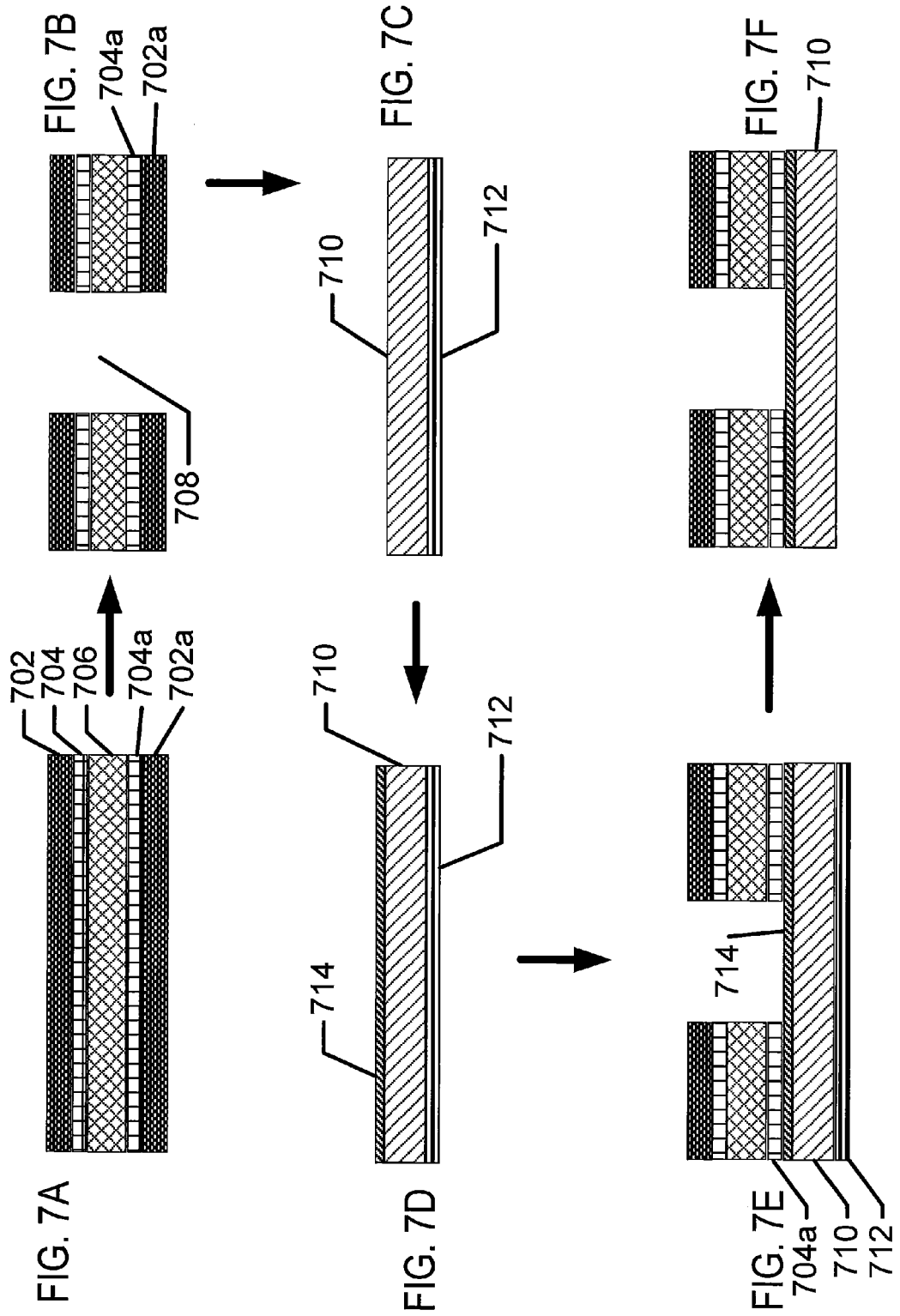

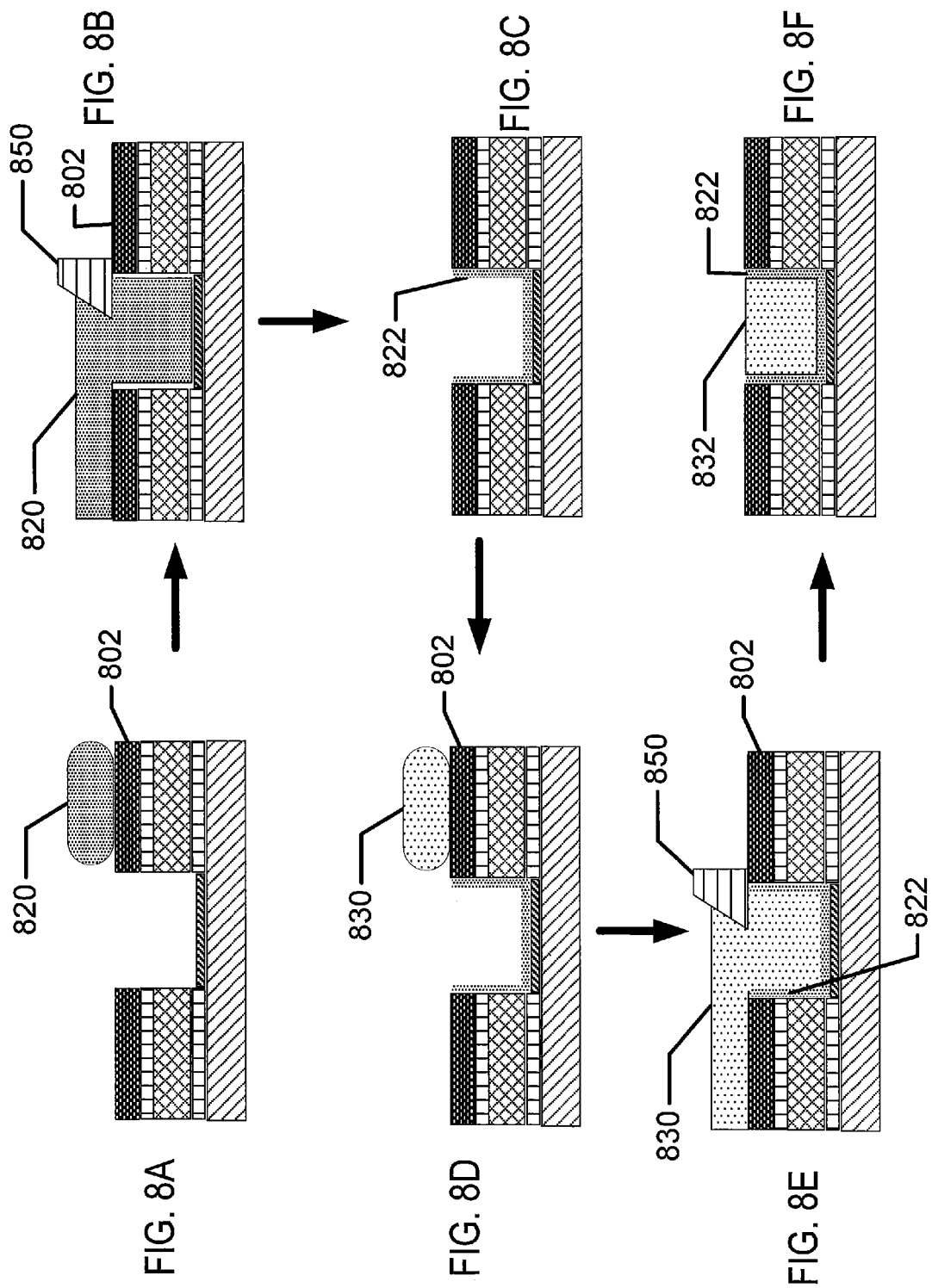

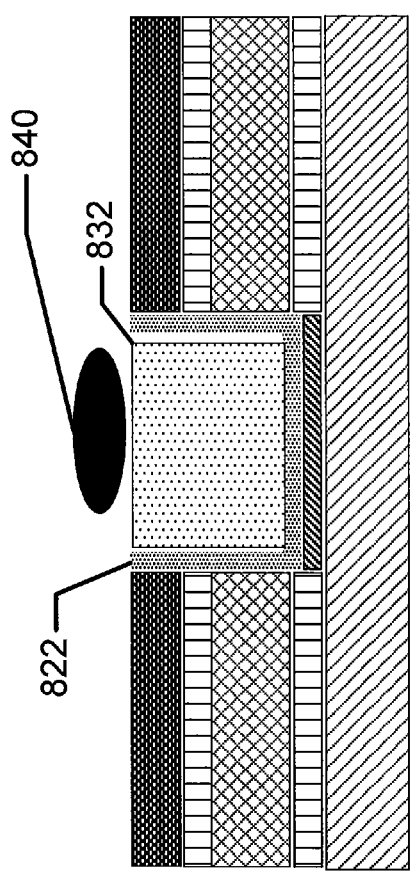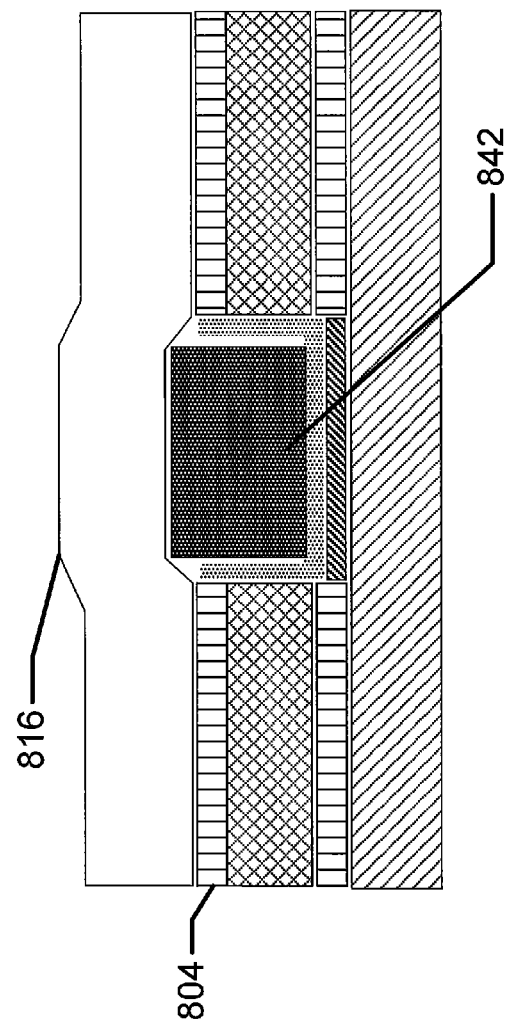

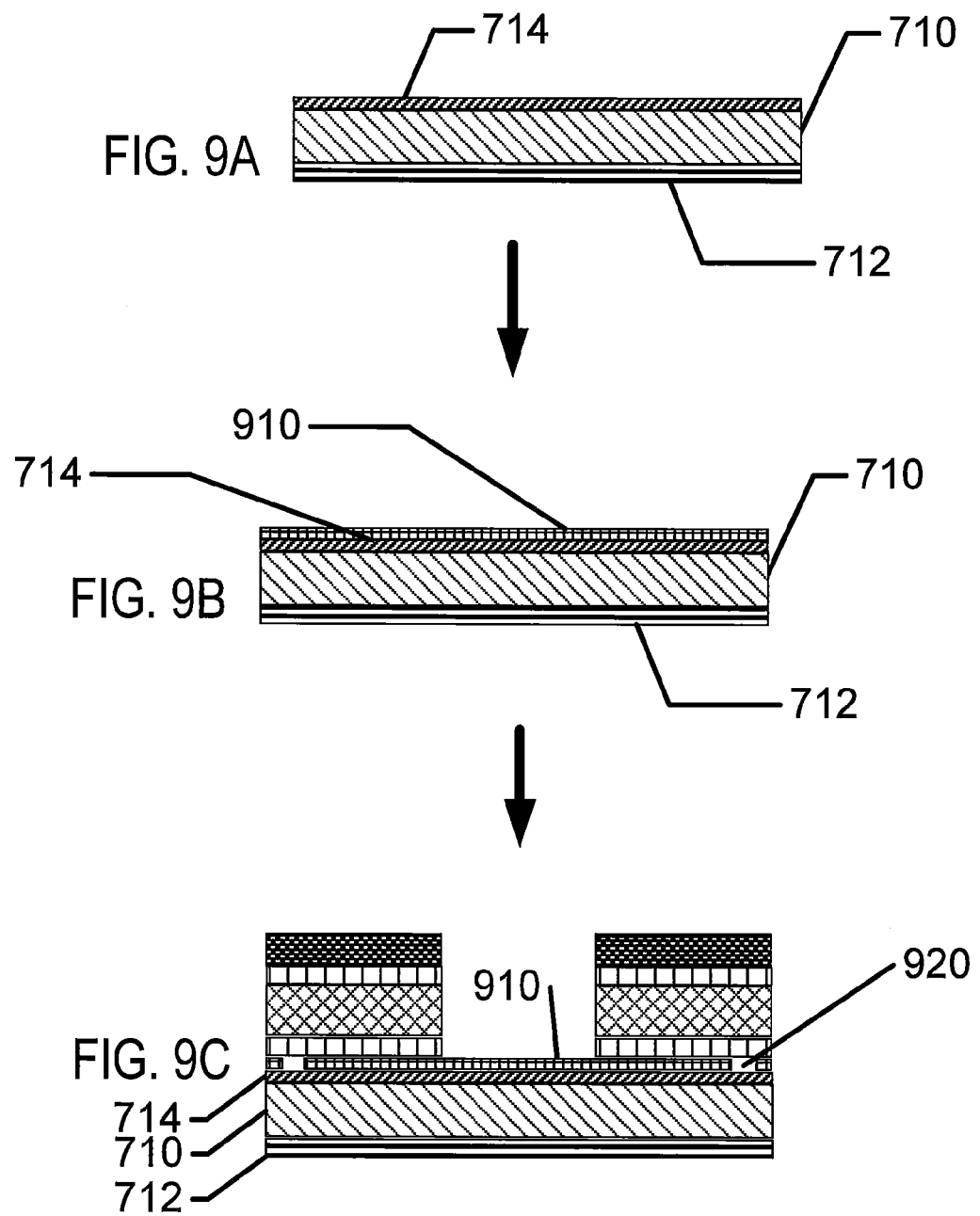

METHODS TO FORM BIOCOMPATIBLE ENERGIZATION ELEMENTS FOR BIOMEDICAL DEVICES COMPRISING LAMINATES AND DEPOSITED SEPARATORS

CROSS REFERENCE TO RELATED APPLICATIONS

This patent application claims the benefit of U.S. Provisional Application No. 62/040,178 filed Aug. 21, 2014 and entitled METHODS AND APPARATUS TO FORM BIOCOMPATIBLE ENERGIZATION ELEMENTS FOR BIOMEDICAL DEVICES. The contents are relied upon and hereby incorporated by reference.

BACKGROUND OF THE INVENTION

1. Field of the Invention

Methods and apparatus to form biocompatible energization elements are described. In some examples, the methods and apparatus to form the biocompatible energization elements involve forming a separator element of the energization element. The active elements, including anodes, cathodes and electrolytes may be electrochemically connected and may interact with the formed separator elements. In some examples, a field of use for the methods and apparatus may include any biocompatible device or product that requires energization elements.

2. Discussion of the Related Art

Recently, the number of medical devices and their functionality has begun to rapidly develop. These medical devices may include, for example, implantable pacemakers, electronic pills for monitoring and/or testing a biological function, surgical devices with active components, contact lenses, infusion pumps, and neurostimulators. Added functionality and an increase in performance to many of the aforementioned medical devices has been theorized and developed. However, to achieve the theorized added functionality, many of these devices now require self-contained energization means that are compatible with the size and shape requirements of these devices, as well as the energy requirements of the new energized components.

Some medical devices may include components such as semiconductor devices that perform a variety of functions and may be incorporated into many biocompatible and/or implantable devices. However, such semiconductor components require energy and, thus, energization elements should preferably also be included in such biocompatible devices. The topology and relatively small size of the biocompatible devices creates novel and challenging environments for the enablement of various functionalities. In many examples, it is important to provide safe, reliable, compact and cost effective means to energize the semiconductor components within the biocompatible devices. Therefore, a need exists for novel examples of forming biocompatible energization elements for implantation within or upon biocompatible devices where the structure of the battery elements provides enhanced containment for chemical components of the energization elements as well as improved control over the quantity of chemical components contained in the energization element.

SUMMARY OF THE INVENTION

Accordingly, methods and apparatus to form biocompatible energization elements are disclosed which afford manufacturing advantages while creating structures which may significantly contain the battery chemistry. As well, the structural design may also provide for inherent control of the quantities of the energization elements found within the battery elements.

One general aspect includes a method of forming a biocompatible energization element, the method including receiving a first substrate film of a first insulating material. The method includes cutting a cavity in the first substrate film to form a cathode spacer layer, where an edge of the cavity defines a sidewall of the cavity. The method includes receiving an anode film and adhering a first surface of the cathode spacer layer to a first surface of the anode film. The method also includes depositing a separator into the biocompatible energization element through the cavity in the cathode spacer layer. Further, the method includes receiving a cathode slurry and placing the cathode slurry into the cavity in the cathode spacer layer. In some examples, the sidewall of the cavity in the cathode spacer layer and a surface of the deposited separator form a bounded cavity to contain the cathode slurry.

Implementations may include one or more additional features. The method may additionally include receiving a cathode contact film and adhering a second surface of the cathode spacer layer to at least a portion of a first surface of the cathode contact film. The method may also include receiving a first packaging film including a film stack where one layer is a metallic moisture barrier and adhering the first packaging film to at least a portion of a second surface of the cathode contact film. In some examples, the method includes receiving a second packaging film including a film stack where one film layer is a metallic moisture barrier and adhering the second packaging film to at least a portion of a second surface of the anode film. The method may additionally include adhering the biocompatible energization element to a portion of a biomedical device, where the cathode slurry is contained at least partially by the sidewall of the cavity in the cathode spacer layer, by the first packaging film and by the second packaging film.

In some examples, the method may include steps where the biocompatible energization element is added to an insert of a biomedical device and where the biocompatible energization element is sealed within the insert, where the cathode slurry is contained at least partially by the sidewall of the cavity in the cathode spacer layer and by the insert. The method may also be characterized where the biomedical device is a contact lens.

In some examples, the method may additionally include adding an electrolyte formulation upon the separator. In some of these examples, the method may additionally include methods where the adding of the electrolyte formulation upon the separator is performed before the placing of the cathode slurry.

In some examples, the method may be characterized in that the cathode slurry includes manganese dioxide. The method may include examples where the manganese dioxide includes electrolytic manganese dioxide. In some examples, the methodology may additionally include processing of the cathode slurry to remove large particulates. When the processing includes removing large particles, the particle sizes may be less than approximately 70 microns. In some examples, the bulk of the particles may have sizes that are less than approximately 25 microns. Processing to remove large particulates may include ball milling. In some other examples, the method to remove large particulates includes jet milling.

The methods may include examples where the first substrate film is polyethylene terephthalate (PET).

In some examples, the method for cutting the cavity in the first substrate film utilizes a laser.

The method may include examples where adhering includes activating a pressure-sensitive adhesive.

In some examples, the method includes cutting multiple cavities into the cathode spacer layer where additionally the separator may deposited into at least two of the multiple cavities.

The method may include electroplating a zinc layer upon the anode film before adhering the first surface of the anode to the first surface of the cathode spacer layer, where the surface of the electroplated zinc layer subsequently becomes the first surface of the anode film.

In some examples, the method additionally includes electrically contacting the biocompatible energization element to an electronic circuit, and electrically contacting the electronic circuit to an electroactive element of a biomedical device.

In some examples, the method may also include bending the device, including the energization element, an electrical circuit, and connections to an electroactive element of the biomedical device. The bending may form a conical-shaped piece by joining, physically and electrically, two ends of the device including, the energization element, an electrical circuit, and connections to an electroactive element of the biomedical device.

One general aspect includes a method of forming a biocompatible energization element, the method including: receiving a first substrate film of a first insulating material; cutting a cavity in the first substrate film to form a cathode spacer layer, where an edge of the cavity defines a sidewall of the cavity; receiving an anode film; depositing a separator onto a first surface of the anode film; adhering a first surface of the cathode spacer layer to a first surface of the deposited separator; receiving a cathode slurry; and placing the cathode slurry into the cavity in the cathode spacer layer, where the sidewall of the cavity in the cathode spacer layer and the first surface of the deposited separator contain the cathode slurry.

BRIEF DESCRIPTION OF THE DRAWINGS

The foregoing and other features and advantages of the invention will be apparent from the following, more particular description of preferred embodiments of the invention, as illustrated in the accompanying drawings.

FIGS. 1A-1D illustrate exemplary aspects of biocompatible energization elements in concert with the exemplary application of contact lenses.

FIG. 3A illustrates a first stand-alone, packaged biocompatible energization element with exemplary anode and cathode connections.

FIG. 3B illustrates a second stand-alone, packaged biocompatible energization element with exemplary anode and cathode connections.

FIGS. 4A-4N illustrate exemplary method steps for the formation of biocompatible energization elements for biomedical devices.

FIGS. 6A-6F illustrate exemplary method steps for structural formation of biocompatible energization elements.

FIGS. 7A-7F illustrate exemplary method steps for structural formation of biocompatible energization elements utilizing an alternate electroplating method.

FIGS. 8A-8H illustrate exemplary method steps for the formation of biocompatible energization elements with hydrogel separator for biomedical devices.

FIGS. 9A-C illustrate exemplary methods steps for structural formation of biocompatible energization elements with alternative separator processing examples.

DETAILED DESCRIPTION OF THE INVENTION

Figure 1C:
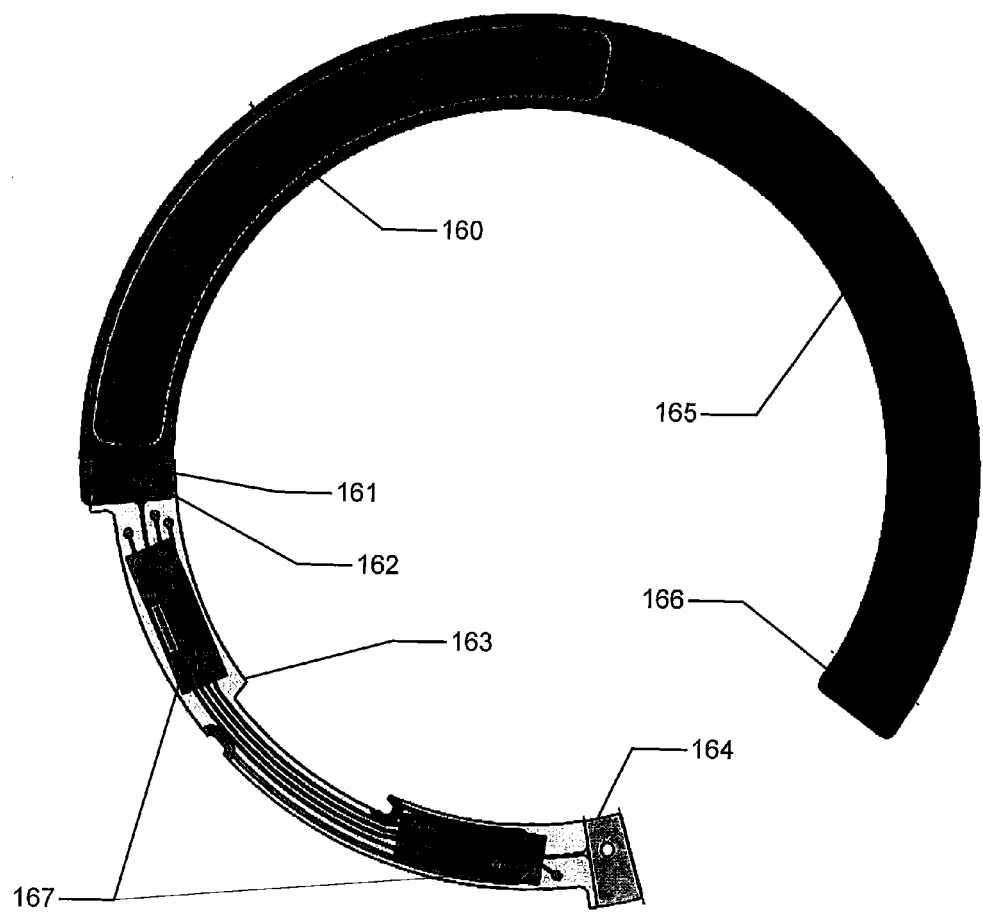

Methods and apparatus to form three-dimensional (3D) biocompatible energization elements are disclosed in this application. The separator element within the energization elements may be formed in novel manners and may include novel materials. In the following sections, detailed descriptions of various examples are described. The descriptions of examples are exemplary embodiments only, and various modifications and alterations may be apparent to those skilled in the art. Therefore, the examples do not limit the scope of this application. The three-dimensional biocompatible energization elements are designed for use in or proximate to the body of a living organism.

Glossary

In the description and claims below, various terms may be used for which the following definitions will apply:

"Anode" as used herein refers to an electrode through which electric current flows into a polarized electrical device. The direction of electric current is typically opposite to the direction of electron flow. In other words, the electrons flow from the anode into, for example, an electrical circuit.

"Binders" as used herein refer to a polymer that is capable of exhibiting elastic responses to mechanical deformations and that is chemically compatible with other energization element components. For example, binders may include electroactive materials, electrolytes, current collectors, etc.

"Biocompatible" as used herein refers to a material or device that performs with an appropriate host response in a specific application. For example, a biocompatible device does not have toxic or injurious effects on biological systems.

"Cathode" as used herein refers to an electrode through which electric current flows out of a polarized electrical device. The direction of electric current is typically opposite to the direction of electron flow. Therefore, the electrons flow into the cathode of the polarized electrical device and out of, for example, the connected electrical circuit.

"Coating" as used herein refers to a deposit of material in thin forms. In some uses, the term will refer to a thin deposit that substantially covers the surface of a substrate it is formed upon. In other more specialized uses, the term may be used to describe small thin deposits in smaller regions of the surface.

"Electrode" as used herein may refer to an active mass in the energy source. For example, it may include one or both of the anode and cathode.

"Energized" as used herein refers to the state of being able to supply electrical current or to have electrical energy stored within.

"Energy" as used herein refers to the capacity of a physical system to do work. Many uses of the energization elements may relate to the capacity of being able to perform electrical actions.

"Energy Source" or "Energization Element" or "Energization Device" as used herein refers to any device or layer which is capable of supplying energy or placing a logical or electrical device in an energized state. The energization elements may include batteries. The batteries may be formed from alkaline type cell chemistry and may be solid-state batteries or wet cell batteries.

"Fillers" as used herein refer to one or more energization element separators that do not react with either acid or alkaline electrolytes. Generally, fillers may include substantially water insoluble materials such as carbon black; coal dust; graphite; metal oxides and hydroxides such as those of silicon, aluminum, calcium, magnesium, barium, titanium, iron, zinc, and tin; metal carbonates such as those of calcium and magnesium; minerals such as mica, montmorollonite, kaolinite, attapulgite, and talc; synthetic and natural zeolites such as Portland cement; precipitated metal silicates such as calcium silicate; hollow or solid polymer or glass microspheres, flakes and fibers; etc.

"Film" as used herein refers to a thin layer of a material that may act as a covering or a coating; in laminate structures the film typically approximates a planar layer with a top surface and a bottom surface and a body; wherein the body is typically much thinner than the extent of the layer.

"Functionalized" as used herein refers to making a layer or device able to perform a function including for example, energization, activation, and/or control.

"Mold" as used herein refers to a rigid or semi-rigid object that may be used to form three-dimensional objects from uncured formulations. Some exemplary molds include two mold parts that, when opposed to one another, define the structure of a three-dimensional object.

"Power" as used herein refers to work done or energy transferred per unit of time.

"Rechargeable" or "Re-energizable" as used herein refer to a capability of being restored to a state with higher capacity to do work. Many uses may relate to the capability of being restored with the ability to flow electrical current at a certain rate for certain, reestablished time periods.

"Reenergize" or "Recharge" as used herein refer to restoring to a state with higher capacity to do work. Many uses may relate to restoring a device to the capability to flow electrical current at a certain rate for a certain, reestablished time period.

"Released" as used herein and sometimes referred to as "released from a mold" means that a three-dimensional object is either completely separated from the mold, or is only loosely attached to the mold, so that it may be removed with mild agitation.

"Stacked" as used herein means to place at least two component layers in proximity to each other such that at least a portion of one surface of one of the layers contacts a first surface of a second layer. In some embodiments, a coating, whether for adhesion or other functions, may reside between the two layers that are in contact with each other through the coating.

"Traces" as used herein refer to energization element components capable of connecting together the circuit components. For example, circuit traces may include copper or gold when the substrate is a printed circuit board and may typically be copper, gold or printed film in a flexible circuit. A special type of "Trace" is the current collector. Current collectors are traces with electrochemical compatibility that makes the current collector suitable for use in conducting electrons to and from an anode or cathode in the presence of electrolyte.

The methods and apparatus presented herein relate to forming biocompatible energization elements for inclusion within or on flat or three-dimensional biocompatible devices. A particular class of energization elements may be batteries that are fabricated in layers. The layers may also be classified as laminate layers. A battery formed in this manner may be classified as a laminar battery.

There may be other examples of how to assemble and configure batteries according to the present invention, and some may be described in following sections. However, for many of these examples, there are selected parameters and characteristics of the batteries that may be described in their own right. In the following sections, some characteristics and parameters will be focused upon.

Exemplary Biomedical Device Construction with Biocompatible Energization Elements An example of a biomedical device that may incorporate the Energization Elements, batteries, of the present invention may be an electroactive focal-adjusting contact lens. Referring to FIG. 1A, an example of such a contact lens insert may be depicted as contact lens insert 100. In the contact lens insert 100, there may be an electroactive element 120 that may accommodate focal characteristic changes in response to controlling voltages. The circuit 105 to provide those controlling voltage signals as well as to provide other function such as controlling sensing of the environment for external control signals may be powered by a biocompatible battery element 110. As depicted in FIG. 1A, the battery element 110 may be found as multiple major pieces, in this case three pieces, and may include the various configurations of battery chemistry elements as has been discussed. The battery elements 110 may have various interconnect features to join together pieces as may be depicted underlying the region of interconnect 114. The battery elements may be connected to a circuit element that may have its own substrate 111 upon which interconnect features 125 may be located. The circuit 105, which may be in the form of an integrated circuit, may be electrically and physically connected to the substrate 111 and its interconnect features 125.

Referring to FIG. 1B, a cross sectional relief of a contact lens 150 may contain contact lens insert 100 and its discussed constituents. The contact lens insert 100 may be encapsulated into a skirt of contact lens hydrogel 155 which may form encapsulate the insert and provide a comfortable interface of the contact lens 150 to a user's eye.

Figure 1D:
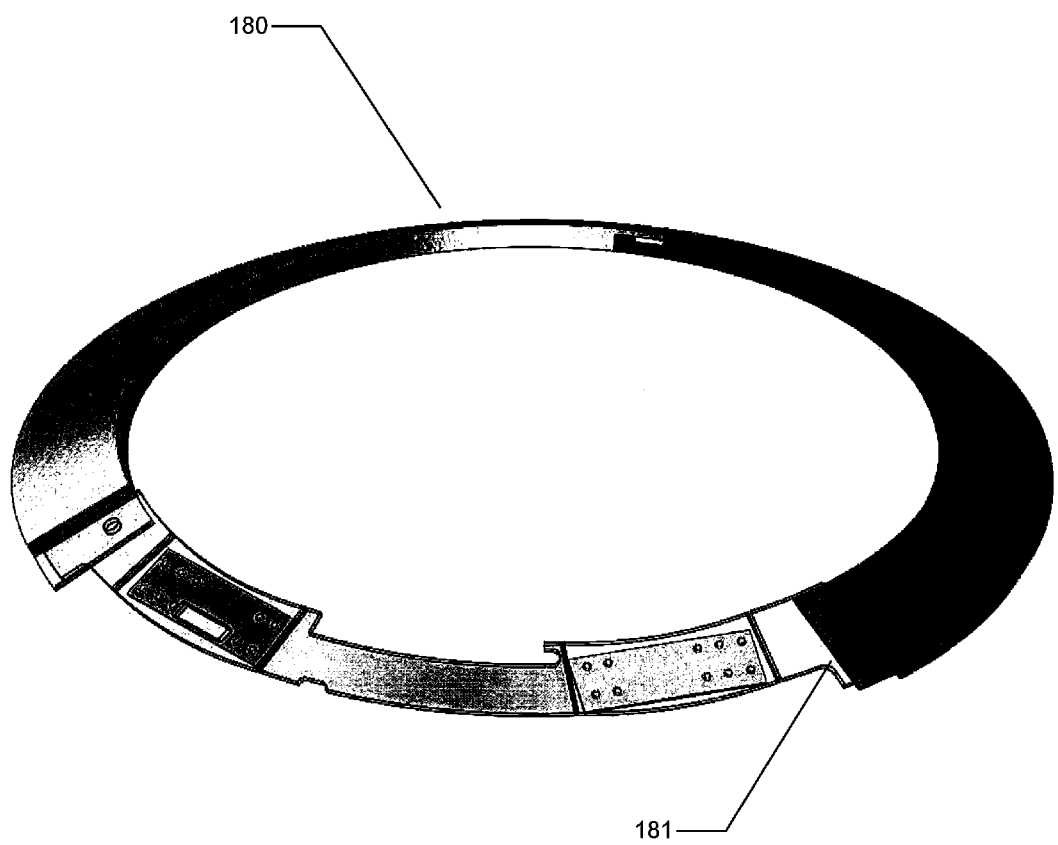

In reference to concepts of the present invention, the battery elements may be formed in a two-dimensional (2D) form as depicted in another example of FIG. 1C. In this depiction there may be two main regions of battery cells in the regions of battery component 165 and the second battery component in the region of battery chemistry element 160. The battery elements, which are depicted in flat form in FIG. 1C, may connect to a circuit element 163, which in the example of FIG. 1C may contain two major circuit areas 167. The circuit element 163 may connect to the battery element at an electrical contact 161 and a physical contact 162. The flat structure may be bent into a three-dimensional conical structure as has been described in the present invention. In that process a second electrical contact 166 and a second physical contact 164 may be used to connect and physically stabilize the three-dimensional structure. Referring to FIG. 1D, a representation of this three-dimensional conical structure 180 may be found. The physical and electrical contact points 181 may also be found and the illustration may be viewed as a three-dimensional view of the resulting structure. This structure may include the modular electrical and battery component that will be incorporated with a lens insert into a biocompatible device.

Segmented Battery Schemes

Figure 2:
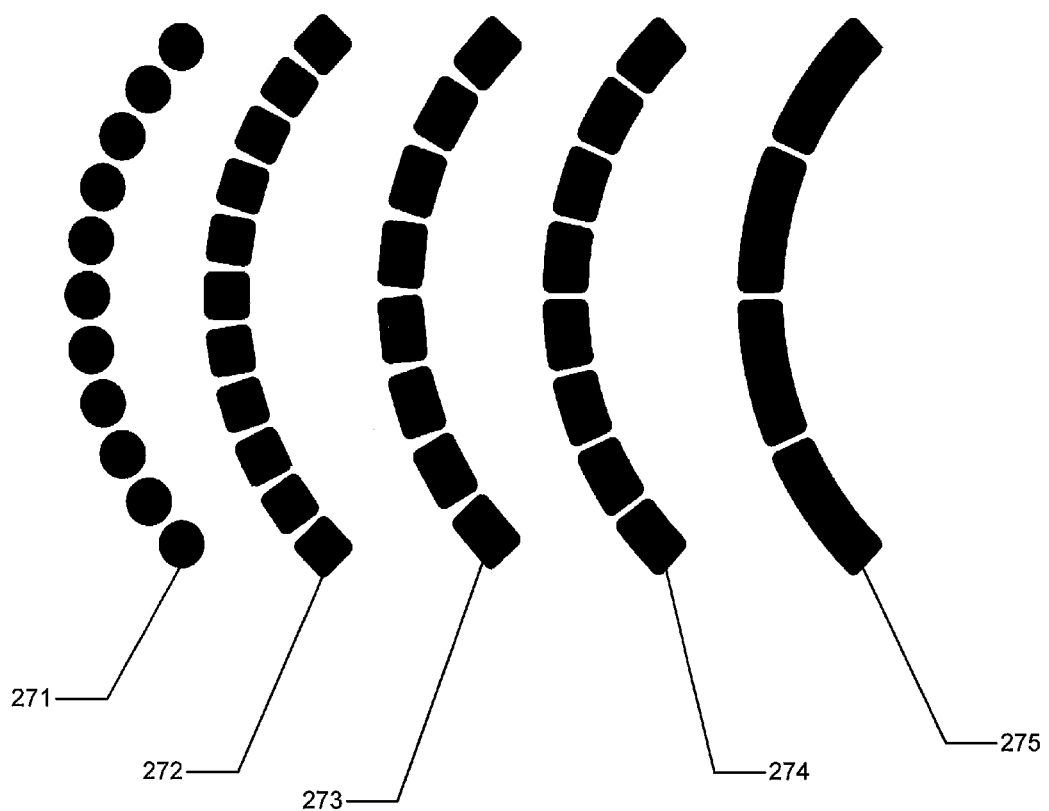
FIG. 2 illustrates the exemplary size and shape of individual cells of an exemplary battery design.

Referring to FIG. 2, an example of different types of segmented battery schemes is depicted for an exemplary battery element for a contact lens type example. The segmented components may be relatively circular-shaped 271, square-shaped 272 or rectangular-shaped. In rectangular-shaped examples, the rectangles may be small rectangular shapes 273, larger rectangular shapes 274, or even larger rectangular shapes 275.

Custom Shapes of Flat Battery Elements

In some examples of biocompatible batteries, the batteries may be formed as flat elements. Referring to FIG. 3A an example of a rectangular outline 310 of the battery element may be depicted with an anode connection 311 and a cathode connection 312. Referring to FIG. 3B an example of a circular outline 330 of a battery element may be depicted with an anode connection 331 and a cathode connection 332.

In some examples of flat-formed batteries, the outlines of the battery form may be dimensionally and geometrically configured to fit in custom products. In addition to examples with rectangular or circular outlines, custom "free-form" or "free shape" outlines may be formed which may allow the battery configuration to be optimized to fit within a given product.

In the exemplary biomedical device case of a variable optic, a "free-form" example of a flat outline may be arcuate in form. The free form may be of such geometry that when formed to a three-dimensional shape, it may take the form of a conical, annular skirt that fits within the constraining confines of a contact lens. It may be clear that similar beneficial geometries may be formed where medical devices have restrictive 2D or 3D shape requirements.

Biocompatibility Aspects of Batteries

As an example, the batteries according to the present invention may have important aspects relating to safety and biocompatibility. In some examples, batteries for biomedical devices should preferably meet requirements above and beyond those for typical usage scenarios. In some examples, design aspects may be considered related to stressing events. For example, the safety of an electronic contact lens may need to be considered in the event a user breaks the lens during insertion or removal. In another example, design aspects may consider the potential for a user to be struck in the eye by a foreign object. Still further examples of stressful conditions that may be considered in developing design parameters and constraints may relate to the potential for a user to wear the lens in challenging environments like the environment under water or the environment at high altitude in non-limiting examples.

The safety of such a device may be influenced by the materials that the device is formed with, by the quantities of those materials employed in manufacturing the device, and also by the packaging applied to separate the devices from the surrounding on- or in-body environment. In an example, pacemakers may be a typical type of biomedical device which may include a battery and which may be implanted in a user for an extended period of time. Accordingly, in some examples, such pacemakers may typically be packaged with welded, hermetic titanium enclosures, or in other examples, multiple layers of encapsulation. Emerging powered biomedical devices may present new challenges for packaging, especially battery packaging. These new devices may be much smaller than existing biomedical devices, for example, an electronic contact lens or pill camera may be significantly smaller than a pacemaker. In such examples, the volume and area available for packaging may be greatly reduced.

Electrical Requirements of Microbatteries

Another area for design considerations may relate to electrical requirements of the device upon the battery device. In order to function as a power source for a medical device, an appropriate battery may need to meet the full electrical requirements of the system when operating in a non-connected or non-externally powered mode. An emerging field of non-connected or non-externally powered biomedical devices may include, for example, vision-correcting contact lenses, health monitoring devices, pill cameras, and novelty devices. Recent developments in integrated circuit (IC) technology may permit meaningful electrical operation at very low current levels, for example, picoamps of standby current and microamps of operating current. IC's may also permit very small devices.

Microbatteries for biomedical applications may be required to meet many simultaneous, challenging requirements. For example, the microbattery may be required to have the capability to deliver a suitable operating voltage to an incorporated electrical circuit. This operating voltage may be influenced by several factors including the IC process "node," the output voltage from the circuit to another device, and a particular current consumption target which may also relate to a desired device lifetime.

With respect to the IC process, nodes may typically be differentiated by the minimum feature size of a transistor, such as its "so-called" transistor channel. This physical feature, along with other parameters of the IC fabrication such as gate oxide thickness, may be associated with a resulting rating standard for "turn-on" or "threshold" voltages of field-effect transistors (FET's) fabricated in the given process node. For example, in a node with a minimum feature size of 0.5 microns it may be common to find FET's with turn-on voltages of 5.0V. However, at a minimum feature size of 90 nm the FET's may turn-on at 1.2, 1.8, and 2.5V. The IC foundry may supply standard cells of digital blocks, for example, inverters and flip-flops that have been characterized and are rated for use over certain voltage ranges. Designers chose an IC process node based on several factors including density of digital devices, analog/digital mixed signal devices, leakage current, wiring layers, and availability of specialty devices such as high-voltage FET's. Given these parametric aspects of the electrical components which may draw power from a microbattery, it may be important for the microbattery power source to be matched to the requirements of the chosen process node and IC design, especially in terms of available voltage and current.

In some examples, an electrical circuit powered by a microbattery, may connect to another device. In non-limiting examples, the microbattery-powered electrical circuit may connect to an actuator or a transducer. Depending on the application, these may include a light-emitting diode (LED), a sensor, a microelectromechanical system (MEMS) pump, or numerous other such devices. In some examples, such connected devices may require higher operating voltage conditions than common IC process nodes, for example, a variable-focus lens may require 35V to activate. The operating voltage provided by the battery may therefore be a critical consideration when designing such a system. In some examples of this type of consideration, the efficiency of a lens driver to produce 35V from a 1V battery may be significantly less than it might be when operating from a 2V battery. Further requirements such as die size may be dramatically different considering the operating parameters of the microbattery as well.

Individual battery cells may typically be rated with open-circuit, loaded, and cutoff voltages. The open-circuit voltage is the potential produced by the battery cell with infinite load resistance. The loaded voltage is the potential produced by the cell with an appropriate, and typically also specified, load impedance placed across the cell terminals. The cutoff voltage is typically a voltage at which most of the battery has been discharged. The cutoff voltage may represent a voltage, or degree of discharge, below which the battery should not be discharged to avoid deleterious effects such as excessive gassing. The cutoff voltage may typically be influenced by the circuit to which the battery is connected, not just the battery itself, for example, the minimum operating voltage of the electronic circuit. In one example, an alkaline cell may have an open-circuit voltage of 1.6V, a loaded voltage in the range 1.0 to 1.5V, and a cutoff voltage of 1.0V. The voltage of a given microbattery cell design may depend upon other factors of the cell chemistry employed. And, different cell chemistry may therefore have different cell voltages.

Cells may be connected in series to increase voltage; however, this combination may come with tradeoffs to size, internal resistance, and battery complexity. Cells may also be combined in parallel configurations to decrease resistance and increase capacity, however such a combination may tradeoff size and shelf life.

Battery capacity may be the ability of a battery to deliver current, or do work, for a period of time. Battery capacity may typically be specified in units such as microamp-hours. A battery which may deliver 1 microamp of current for 1 hour has 1 microamp-hour of capacity. Capacity may typically be increased by increasing the mass (and hence volume) of reactants within a battery device; however, it may be appreciated that biomedical devices may be significantly constrained on available volume. Battery capacity may also be influenced by electrode and electrolyte material.

Depending on the requirements of the circuitry to which the battery is connected, a battery may be required to source current over a range of values. During storage prior to active use, a leakage current on the order of picoamps to nanoamps may flow through circuits, interconnects, and insulators. During active operation, circuitry may consume quiescent current to sample sensors, run timers, and perform such low power consumption functions. Quiescent current consumption may be on the order of nanoamps to milliamps. Circuitry may also have even higher peak current demands, for example, when writing flash memory or communicating over radio frequency (RF). This peak current may extend to tens of milliamps or more. The resistance and impedance of a microbattery device may also be important to design considerations.

Shelf life typically refers to the period of time which a battery may survive in storage and still maintain useful operating parameters. Shelf life may be particularly important for biomedical devices for several reasons. Electronic devices may displace non-powered devices, as for example may be the case for the introduction of an electronic contact lens. Products in these existing market spaces may have established shelf life requirements, for example, three years, due to customer, supply chain, and other requirements. It may typically be desired that such specifications not be altered for new products. Shelf life requirements may also be set by the distribution, inventory, and use methods of a device including a microbattery. Accordingly, microbatteries for biomedical devices may have specific shelf life requirements, which may be measured in the number of years for example.

In some examples, three-dimensional biocompatible energization element may be rechargeable. For example, an inductive coil may also be fabricated on the three-dimensional surface. The inductive coil could then be energized with a radio-frequency ("RF") fob. The inductive coil may be connected to the three-dimensional biocompatible energization element to recharge the energization element when RF is applied to the inductive coil. In another example, photovoltaics may also be fabricated on the three-dimensional surface and connected to the three-dimensional biocompatible energization element. When exposed to light or photons, the photovoltaics will produce electrons to recharge the energization element.

In some examples, a battery may function to provide the electrical energy for an electrical system. In these examples, the battery may be electrically connected to the circuit of the electrical system. The connections between a circuit and a battery may be classified as interconnects. These interconnects may become increasingly challenging for biomedical microbatteries due to several factors. In some examples, powered biomedical devices may be very small thus allowing little area and volume for the interconnects. The restrictions of size and area may impact the electrical resistance and reliability of the interconnections.

In other respects, a battery may contain a liquid electrolyte which could boil at high temperature. This restriction may directly compete with the desire to use a solder interconnect which may, for example, require relatively high temperatures such as 250 degrees C. to melt. Although in some examples the battery chemistry, including the electrolyte, and the heat source used to form solder based interconnects may be isolated spatially from each other, in the cases of emerging biomedical devices, the small size may preclude the separation of electrolyte and solder joints by sufficient distance to reduce heat conduction.

Interconnects

Interconnects may allow current to flow to and from the battery in connection with an external circuit. Such interconnects may interface with the environments inside and outside the battery, and may cross the boundary or seal between those environments. These interconnects may be considered as traces, making connections to an external circuit, passing through the battery seal, and then connecting to the current collectors inside the battery. As such, these interconnects may have several requirements. Outside the battery, the interconnects may resemble typical printed circuit traces. They may be soldered to or otherwise connect to other traces. In an example where the battery is a separate physical element from a circuit board containing an integrated circuit, the battery interconnect may allow for connection to the external circuit. This connection may be formed with solder, conductive tape, conductive ink or epoxy, or other means. The interconnect traces may need to survive in the environment outside the battery, for example, not corroding in the presence of oxygen.

As the interconnect passes through the battery seal, it may be of critical importance that the interconnect coexist with the seal and permit sealing. Adhesion may be required between the seal and interconnect in addition to the adhesion which may be required between the seal and battery package. Seal integrity may need to be maintained in the presence of electrolyte and other materials inside the battery. Interconnects, which may typically be metallic, may be known as points of failure in battery packaging. The electrical potential and/or flow of current may increase the tendency for electrolyte to "creep" along the interconnect. Accordingly, an interconnect may need to be engineered to maintain seal integrity.

Inside the battery, the interconnects may interface with the current collectors or may actually form the current collectors. In this regard, the interconnect may need to meet the requirements of the current collectors as described herein, or may need to form an electrical connection to such current collectors.

One class of candidate interconnects and current collectors is metal foils. Such foils are available in thickness of 25 microns or less, which make them suitable for very thin batteries. Such foil may also be sourced with low surface roughness and contamination, two factors which may be critical for battery performance. The foils may include zinc, nickel, brass, copper, titanium, other metals, and various alloys.

Electrolyte

An electrolyte is a component of a battery which facilitates a chemical reaction to take place between the chemical materials of the electrodes. Typical electrolytes may be electrochemically active to the electrodes, for example, allowing oxidation and reduction reactions to occur. In some examples, this important electrochemical activity may make for a challenge to creating devices that are biocompatible. For example, potassium hydroxide (KOH) may be a commonly used electrolyte in alkaline cells. At high concentration the material has a high pH and may interact unfavorably with various living tissues. On the other hand, in some examples electrolytes may be employed which may be less electrochemically active; however, these materials may typically result in reduced electrical performance, such as reduced cell voltage and increased cell resistance. Additionally, it may be desirable for the electrolyte to be compatible. Accordingly, one key aspect of the design and engineering of a biomedical microbattery may be the electrolyte. It may be desirable for the electrolyte to be sufficiently active to meet electrical requirements while also being relatively safe for use in- or on-body.

Various test scenarios may be used to determine the safety of battery components, in particular electrolytes, to living cells. These results, in conjunction with tests of the battery packaging, may allow engineering design of a battery system that may meet requirements. For example, when developing a powered contact lens, battery electrolytes may be tested on a human corneal cell model. These tests may include experiments on electrolyte concentration, exposure time, and additives. The results of such tests may indicate cell metabolism and other physiological aspects. Tests may also include in-vivo testing on animals and humans.

Electrolytes for use in the present invention may include zinc chloride, zinc acetate, ammonium acetate, and ammonium chloride in mass concentrations from approximately 0.1 percent to 50 percent, and in a non-limiting example may be approximately 25 percent. The specific concentrations may depend on electrochemical activity, battery performance, shelf life, seal integrity, and biocompatibility.

In some examples, several classes of additives may be utilized in the composition of a battery system. Additives may be mixed into the electrolyte base to alter its characteristics. For example, gelling agents such as agar may reduce the ability of the electrolyte to leak out of packing, thereby increasing safety. Corrosion inhibitors may be added to the electrolyte, for example, to improve shelf life by reducing the undesired dissolution of the zinc anode into the electrolyte. These inhibitors may positively or adversely affect the safety profile of the battery. Wetting agents or surfactants may be added, for example, to allow the electrolyte to wet the separator or to be filled into the battery package. Again, these wetting agents may be positive or negative for safety. The addition of surfactant to the electrolyte may increase the electrical impedance of the cell, according the lowest concentration of surfactant to achieve the desired wetting or other properties should be used. Exemplary surfactants may include Triton™ X-100, Triton™ QS44, and Dowfax™ 3B2, all available from the Dow Chemical company, in concentrations from 0.01 percent to 2 percent.

Novel electrolytes are also emerging which may dramatically improve the safety profile of biomedical microbatteries. For example, a class of solid electrolytes may be inherently resistant to leaking while still offering suitable electrical performance.

Batteries using "salt water" electrolyte are commonly used in reserve cells for marine use. Torpedoes, buoys, and emergency lights may use such batteries. Reserve cells are batteries in which the active materials, the electrodes and electrolyte, are separated until the time of use. Because of this separation, the cells' self-discharge is greatly reduced and shelf life is greatly increased. Salt water batteries may be designed from a variety of electrode materials, including zinc, magnesium, aluminum, copper, tin, manganese dioxide, and silver oxide. The electrolyte may be actual sea water, for example, water from the ocean flooding the battery upon contact, or may be a specially engineered saline formulation. This type of battery may be particularly useful in contact lenses. A saline electrolyte may have superior biocompatibility to classical electrolytes such as potassium hydroxide and zinc chloride. Contact lenses are stored in a "packing solution" which is typically a mixture of sodium chloride, perhaps with other salts and buffering agents. This solution has been demonstrated as a battery electrolyte in combination with a zinc anode and manganese dioxide cathode. Other electrolyte and electrode combinations are possible. A contact lens using a "salt water" battery may contain an electrolyte based on sodium chloride, packing solution, or even a specially engineered electrolyte similar to tear fluid. Such a battery could, for example, be activated with packing solution, maintain an opening to the eye, and continue operating with exposure to human tears.

In addition to or instead of possible benefits for biocompatibility by using an electrolyte more similar to tears, or actually using tears, a reserve cell may be used to meet the shelf life requirements of a contact lens product. Typical contact lenses are specified for storage of 3 years or more. This is a challenging requirement for a battery with a small and thin package. A reserve cell for use in a contact lens may have design similar to those shown in FIGS. 1 and 3, but the electrolyte would not be added at the time of manufacture. The electrolyte may be stored in an ampule within the contact lens and connected to the battery, or saline surrounding the battery may be used as the electrolyte. Within the contact lens and battery package, a valve or port may be designed to separate the electrolyte from the electrodes until the user activates the lens. Upon activation, perhaps by simply pinching the edge of the contact lens similar to activating a glow stick, the electrolyte is allowed to flow into the battery and form an ionic pathway between the electrodes. This may involve a one-time transfer of electrolyte or may expose the battery for continued diffusion.

Some battery systems may use or consume electrolyte during the chemical reaction. Accordingly, it may be necessary to engineer a certain volume of electrolyte into the packaged system. This electrolyte may be "parked" in various locations including the separator or a reservoir.

In some examples, a design of a battery system may include a component or components that may function to limit discharge capacity of the battery system. For example, it may be desirable to design the materials and amounts of materials of the anode, cathode, or electrolyte such that one of them may be depleted first during the course of reactions in the battery system. In such an example, the depletion of one of the anode, cathode or electrode may reduce the potential for problematic discharge and side reactions to not take place at lower discharge voltages. These problematic reactions may produce, for example, excessive gas or byproducts which could be detrimental to safety and other factors.

Modular Battery Components

In some examples, a modular battery component may be formed according to some aspects and examples of the present invention. In these examples, the modular battery assembly may be a separate component from other parts of the biomedical device. In the example of an ophthalmic contact lens device, such a design may include a modular battery that is separate from the rest of a media insert. There may be numerous advantages of forming a modular battery component. For example, in the case of the contact lens, a modular battery component may be formed in a separate, non-integrated process which may alleviate the need to handle rigid, three dimensionally formed optical plastic components. In addition, the sources of manufacturing may be more flexible and may operate in a more parallel mode to the manufacturing of the other components in the biomedical device. Furthermore, the fabrication of the modular battery components may be decoupled from the characteristics of three-dimensional shaped devices. For example, in applications requiring three-dimensional final forms, a modular battery system may be fabrication in a flat or roughly two-dimensional perspective and then shaped to the appropriate three-dimensional shape. A modular battery component may be tested independently of the rest of the biomedical device and yield loss due to battery components may be sorted before assembly. The resulting modular battery component may be utilized in various media insert constructs that do not have an appropriate rigid region upon which the battery components may be formed. And, in a still further example, the use of modular battery components may facilitate the use of different options for fabrication technologies than would otherwise be utilized, such as web-based technology (roll to roll), sheet-based technology (sheet-to-sheet), printing, lithography, and "squeegee" processing. In some examples of a modular battery, the discrete containment aspect of such a device may result in additional material being added to the overall biomedical device construct. Such effects may set a constraint for the use of modular battery solutions when the available space parameters require minimized thickness or volume of solutions.

Battery shape requirements may be driven, at least in part, by the application for which the battery is to be used. Traditional battery form factors may be cylindrical forms or rectangular prisms, made of metal, and may be geared toward products which require large amounts of power for long durations. These applications may be large enough that they may contain large form factor batteries. In another example, planar (2D) solid-state batteries are thin rectangular prisms, typically formed upon inflexible silicon or glass. These planar solid-state batteries may be formed in some examples using silicon wafer-processing technologies. In another type of battery form factor, low power, flexible batteries may be formed in a pouch construct, using thin foils or plastic to contain the battery chemistry. These batteries may be made flat (2D), and may be designed to function when bowed to a modest out-of-plane (3D) curvature.

In some of the examples of the battery applications in the present invention where the battery may be employed in a variable optic lens, the form factor may require a three-dimensional curvature of the battery component where a radius of that curvature may be on the order of approximately 8.4 mm. The nature of such a curvature may be considered to be relatively steep and for reference may approximate the type of curvature found on a human fingertip. The nature of a relative steep curvature creates challenging aspects for manufacture. In some examples of the present invention, a modular battery component may be designed such that it may be fabricated in a flat, two-dimensional manner and then formed into a three-dimensional form of relative high curvature.

Battery Module Thickness

In designing battery components for biomedical applications, tradeoffs amongst the various parameters may be made balancing technical, safety and functional requirements. The thickness of the battery component may be an important and limiting parameter. For example, in an optical lens application the ability of a device to be comfortably worn by a user may have a critical dependence on the thickness across the biomedical device. Therefore, there may be critical enabling aspects in designing the battery for thinner results. In some examples, battery thickness may be determined by the combined thicknesses of top and bottom sheets, spacer sheets, and adhesive layer thicknesses. Practical manufacturing aspects may drive certain parameters of film thickness to standard values in available sheet stock. In addition, the films may have minimum thickness values to which they may be specified base upon technical considerations relating to chemical compatibility, moisture/gas impermeability, surface finish, and compatibility with coatings that may be deposited upon the film layers.

In some examples, a desired or goal thickness of a finished battery component may be a component thickness that is less than 220 µm. In these examples, this desired thickness may be driven by the three-dimensional geometry of an exemplary ophthalmic lens device where the battery component may need to be fit inside the available volume defined by a hydrogel lens shape given end user comfort, biocompatibility, and acceptance constraints. This volume and its effect on the needs of battery component thickness may be a function of total device thickness specification as well as device specification relating to its width, cone angle, and inner diameter. Another important design consideration for the resulting battery component design may relate to the volume available for active battery chemicals and materials in a given battery component design with respect to the resulting chemical energy that may result from that design. This resulting chemical energy may then be balanced for the electrical requirements of a functional biomedical device for its targeted life and operating conditions Battery Module Flexibility Another dimension of relevance to battery design and to the design of related devices that utilize battery based energy sources is the flexibility of the battery component. There may be numerous advantages conferred by flexible battery forms. For example, a flexible battery module may facilitate the previously mentioned ability to fabricate the battery form in a two-dimensional (2D) flat form. The flexibility of the form may allow the two-dimensional battery to then be formed into an appropriate 3D shape to fit into a biomedical device such as a contact lens.

In another example of the benefits that may be conferred by flexibility in the battery module, if the battery and the subsequent device is flexible then there may be advantages relating to the use of the device. In an example, a contact lens form of a biomedical device may have advantages for insertion/removal of the media insert based contact lens that may be closer to the insertion/removal of a standard, non-filled hydrogel contact lens.

The number of flexures may be important to the engineering of the battery. For example, a battery which may only flex one time from a planar form into a shape suitable for a contact lens may have significantly different design from a battery capable of multiple flexures. The flexure of the battery may also extend beyond the ability to mechanically survive the flexure event. For example, an electrode may be physically capable of flexing without breaking, but the mechanical and electrochemical properties of the electrode may be altered by flexure. Flex-induced changes may appear instantly, for example, as changes to impedance, or flexure may introduce changes which are only apparent in long-term shelf life testing.

Battery Module Width

There may be numerous applications into which the biocompatible energization elements or batteries of the present invention may be utilized. In general, the battery width requirement may be largely a function of the application in which it is applied. In an exemplary case, a contact lens battery system may have constrained needs for the specification on the width of a modular battery component. In some examples of an ophthalmic device where the device has a variable optic function powered by a battery component, the variable optic portion of the device may occupy a central spherical region of about 7.0 mm in diameter. The exemplary battery elements may be considered as a three-dimensional object, which fits as an annular, conical skirt around the central optic and formed into a truncated conical ring. If the required maximum diameter of the rigid insert is a diameter of 8.50 mm, and tangency to a certain diameter sphere may be targeted (as for example in a roughly 8.40 mm diameter), then geometry may dictate what the allowable battery width may be. There may be geometric models that may be useful for calculating desirable specifications for the resulting geometry which in some examples may be termed a conical frustum flattened into a sector of an annulus.

Flattened battery width may be driven by two features of the battery element, the active battery components and seal width. In some examples relating to ophthalmic devices a target thickness may be between 0.100 mm and 0.500 mm per side, and the active battery components may be targeted at roughly 0.800 mm wide. Other biomedical devices may have differing design constraints but the principles for flexible flat battery elements may apply in similar fashion.

Cavities as Design Elements in Battery Component Design

In some examples, battery elements may be designed in manners that segment the regions of active battery chemistry. There may be numerous advantages from the division of the active battery components into discrete segments. In a non-limiting example, the fabrication of discrete and smaller elements may facilitate production of the elements. The function of battery elements including numerous smaller elements may be improved. Defects of various kinds may be isolated. These isolated non-functional elements, in some cases, may result in decreased loss of function. This may be relevant in examples where the loss of battery electrolyte may occur. The isolation of individualized components may allow for a defect that results in leakage of electrolyte out of the critical regions of the battery to limit the loss of function to that small segment of the total battery element whereas the electrolyte loss through the defect could empty a significantly larger region for batteries configured as a single cell. Smaller cells may result in lowered volume of active battery chemicals on an overall perspective, but the mesh of material surrounding each of the smaller cells may result in a strengthening of the overall structure.

Battery Element Internal Seals

In some examples of battery elements for use in biomedical devices, the chemical action of the battery involves aqueous chemistry, where water or moisture is an important constituent to control. Therefore it may be important to incorporate sealing mechanisms that retard or prevent the movement of moisture either out of or into the battery body. Moisture barriers may be designed to keep the internal moisture level at a designed level, within some tolerance. In some examples, a moisture barrier may be divided into two sections or components: namely, the package and the seal.

The package may refer to the main material of the enclosure. In some examples, the package may comprise a bulk material. The Water Vapor Transmission Rate (WVTR) may be an indicator of performance. Ideally, the WVTR for a good battery package may be "zero." Exemplary materials with a near-zero WVTR may be glass and metal foils. Plastics, on the other hand, may be inherently porous to moisture, and may vary significantly for different types of plastic. Engineered materials, laminates, or co-extrudes may usually be hybrids of the common package materials.

The seal may be the interface between two of the package surfaces. The connecting of seal surfaces finishes the enclosure along with the package. In many examples, the nature of seal designs may make them difficult to characterize for the seal's WVTR due to difficulty in performing measurements using an ISO or ASTM standard, as the sample size or surface area may not be compatible with those procedures. In some examples, a practical manner to testing seal integrity may be a functional test of the actual seal design, for some defined conditions. Seal performance may be a function of the seal material, the seal thickness, the seal length, the seal width, and the seal adhesion or intimacy to package substrates.

In some examples, seals may be formed by a welding process that may involve thermal, solvent, friction, ultrasonic, or arc processing. In other examples, seals may be formed through the use of adhesive sealants such as glues, epoxies, acrylics, natural rubber, and synthetic rubber. Other examples may derive from the utilization of gasket type material that may be formed from cork, natural and synthetic rubber, polytetrafluoroethylene (PTFE), polypropylene, and silicones to mention a few non-limiting examples.

In some examples, the batteries according to the present invention may be designed to have a specified operating life. The operating life may be estimated by determining a practical amount of moisture permeability that may be obtained using a particular battery system and then estimating when such a moisture leakage may result in an end of life condition for the battery. For example, if a battery is stored in a wet environment, then the partial pressure difference between inside and outside the battery will be minimal, resulting in a reduced moisture loss rate, and therefore the battery life may be extended. The same exemplary battery stored in a particularly dry and hot environment may have a significantly reduced expectable lifetime due to the strong driving function for moisture loss.

Battery Element Separators

Batteries of the type described in the present invention may utilize a separator material that physically and electrically separates the anode and anode current collector portions from the cathode and cathode current collector portions. The separator may be a membrane that is permeable to water and dissolved electrolyte components; however, it may typically be electrically non-conductive. While a myriad of commercially-available separator materials may be known to those of skill in the art, the novel form factor of the present invention may present unique constraints on the task of separator selection, processing, and handling.

Since the designs of the present invention may have ultra-thin profiles, the choice may be limited to the thinnest separator materials typically available. For example, separators of approximately 25 microns in thickness may be desirable. Some examples which may be advantageous may be about 12 microns in thickness. There may be numerous acceptable commercial separators include microfibrillated, microporous polyethylene monolayer and/or polypropylene-polyethylene-polypropylene (PP/PE/PP) trilayer separator membranes such as those produced by Celgard (Charlotte, N.C.). A desirable example of separator material may be Celgard M824 PP/PE/PP trilayer membrane having a thickness of 12 microns. Alternative examples of separator materials useful for examples of the present invention may include separator membranes including regenerated cellulose (e.g. cellophane).

While PP/PE/PP trilayer separator membranes may have advantageous thickness and mechanical properties, owing to their polyolefinic character, they may also suffer from a number of disadvantages that must be overcome in order to make them useful in examples of the present invention. Roll or sheet stock of PP/PE/PP trilayer separator materials may have numerous wrinkles or other form errors that may be deleterious to the micron-level tolerances applicable to the batteries described herein. Furthermore, polyolefin separators may need to be cut to ultra-precise tolerances for inclusion in the present designs, which may therefore implicate laser cutting as one exemplary method of forming discrete current collectors in desirable shapes with tight tolerances. Owing to the polyolefinic character of these separators, certain cutting lasers useful for micro fabrication may employ laser wavelengths, e.g. 355 nm, that will not cut polyolefins. The polyolefins do not appreciably absorb the laser energy and are thereby non-ablatable. Finally, polyolefin separators may not be inherently wettable to aqueous electrolytes used in the batteries described herein.

Nevertheless, there may be methods for overcoming these inherent limitations for polyolefinic type membranes. In order to present a microporous separator membrane to a high-precision cutting laser for cutting pieces into arc segments or other advantageous separator designs, the membrane may need to be flat and wrinkle-free. If these two conditions are not met, the separator membrane may not be fully cut because the cutting beam may be inhibited as a result of defocusing of or otherwise scattering the incident laser energy. Additionally, if the separator membrane is not flat and wrinkle-free, the form accuracy and geometric tolerances of the separator membrane may not be sufficiently achieved. Allowable tolerances for separators of current examples may, for example, be +0 microns and −20 microns with respect to characteristic lengths and/or radii. There may be advantages for tighter tolerances of +0 microns and −10 micron and further for tolerances of +0 microns and −5 microns. Separator stock material may be made flat and wrinkle-free by temporarily laminating the material to a float glass carrier with an appropriate low-volatility liquid. Low-volatility liquids may be advantageous over temporary adhesives due to the fragility of the separator membrane and due to the amount of processing time that may be required to release separator membrane from an adhesive layer. Furthermore, in some examples achieving a flat and wrinkle-free separator membrane on float glass using a liquid has been observed to be much more facile than using an adhesive. Prior to lamination, the separator membrane may be made free of particulates. This may be achieved by ultrasonic cleaning of separator membrane to dislodge any surface-adherent particulates. In some examples, handling of a separator membrane may be done in a suitable, low-particle environment such as a laminar flow hood or a cleanroom of at least class 10,000. Furthermore, the float glass substrate may be made to be particulate free by rinsing with an appropriate solvent, ultrasonic cleaning, and/or wiping with clean room wipes.

While a wide variety of low-volatility liquids may be used for the mechanical purpose of laminating microporous polyolefin separator membranes to a float glass carrier, specific requirements may be imposed on the liquid to facilitate subsequent laser cutting of discrete separator shapes. One requirement may be that the liquid has a surface tension low enough to soak into the pores of the separator material which may easily be verified by visual inspection. In some examples, the separator material turns from a white color to a translucent appearance when liquid fills the micropores of the material. It may be desirable to choose a liquid that may be benign and "safe" for workers whom will be exposed to the preparation and cutting operations of the separator. It may be desirable to choose a liquid whose vapor pressure may be low enough so that appreciable evaporation does not occur during the time scale of processing (on the order of 1 day). The process of infusing low-volatility liquid may be enhanced through the use of pressurization of the fluid. In other examples, vacuum may be used to enhance infusion. Finally, in some examples the liquid may have sufficient solvating power to dissolve advantageous UV absorbers that may facilitate the laser cutting operation. In an example, it has been observed that a 12 percent (w/w) solution of avobenzone UV absorber in benzyl benzoate solvent may meet the aforementioned requirements and may lend itself to facilitating the laser cutting of polyolefin separators with high precision and tolerance in short order without an excessive number of passes of the cutting laser beam. In some examples, separators may be cut with an 8 W 355 nm nanosecond diode-pumped solid state laser using this approach where the laser may have settings for low power attenuation (e.g. 3 percent power), a moderate speed of 1 to 10 mm/s, and only 1 to 3 passes of the laser beam. While this UV-absorbing oily composition has been proven to be an effective laminating and cutting process aid, other oily formulations may be envisaged by those of skill in the art and used without limitation.

In some examples, a separator may be cut while fixed to a float glass. One advantage of laser cutting separators while fixed to a float glass carrier may be that a very high number density of separators may be cut from one separator stock sheet: much like semiconductor die may be densely arrayed on a silicon wafer. Such an approach may provide economy of scale and parallel processing advantages inherent in semiconductor processes. Furthermore, the generation of scrap separator membrane may be minimized. Once separators have been cut, the oily process aid fluid may be removed by a series of extraction steps with miscible solvents, the last extraction may be performed with a highvolatility solvent such as isopropyl alcohol in some examples. Discrete separators, once extracted, may be stored indefinitely in any suitable low-particle environment.

As previously mentioned polyolefin separator membranes may be inherently hydrophobic and may need to be made wettable to aqueous surfactants used in the batteries of the present invention. One approach to make the separator membranes wettable may be oxygen plasma treatment. For example, separators may be treated for 1 to 5 minutes in a 100% oxygen plasma at a wide variety of power settings and oxygen flow rates. While this approach may improve wettability for a time, it may be well-known that plasma surface modifications provide a transient effect that may not last long enough for robust wetting of electrolyte solutions. Another approach to improve wettability of separator membranes may be to treat the surface by incorporating a suitable surfactant on the membrane. In some cases, the surfactant may be used in conjunction with a hydrophilic polymeric coating that remains within the pores of the separator membrane.

Another approach to provide more permanence to the hydrophilicity imparted by an oxidative plasma treatment may be by subsequent treatment with a suitable hydrophilic organosilane. In this manner, the oxygen plasma may be used to activate and impart functional groups across the entire surface area of the microporous separator. The organosilane may then covalently bond to and/or non-covalently adhere to the plasma treated surface. In examples using an organosilane, the inherent porosity of the microporous separator may not be appreciably changed. Monolayer surface coverage may also be possible and desired. Prior art methods incorporating surfactants in conjunction with polymeric coatings may require stringent controls over the actual amount of coating applied to the membrane, and may then be subject to process variability. In extreme cases, pores of the separator may become blocked, thereby adversely affecting utility of the separator during the operation of the electrochemical cell. An exemplary organosilane useful in the present invention may be (3-aminopropyl)triethoxysilane. Other hydrophilic organosilanes may be known to those of skill in the art and may be used without limitation.

Still another method for making separator membranes wettable by aqueous electrolyte may be the incorporation of a suitable surfactant in the electrolyte formulation. One consideration in the choice of surfactant for making separator membranes wettable may be the effect that the surfactant may have on the activity of one or more electrodes within the electrochemical cell, for example, by increasing the electrical impedance of the cell. In some cases, surfactants may have advantageous anti-corrosion properties, specifically in the case of zinc anodes in aqueous electrolytes. Zinc may be an example known to undergo a slow reaction with water to liberate hydrogen gas, which may be undesirable. Numerous surfactants may be known by those of skill in the art to limit rates of the reaction to advantageous levels. In other cases, the surfactant may so strongly interact with the zinc electrode surface that battery performance may be impeded. Consequently, much care may need to be made in the selection of appropriate surfactant types and loading levels to ensure that separator wettability may be obtained without deleteriously affecting electrochemical performance of the cell. In some cases, a plurality of surfactants may be used, one being present to impart wettability to the separator membrane and the other being present to facilitate anti-corrosion properties to the zinc anode. In one example, no hydrophilic treatment is done to the separator membrane and a surfactant or plurality of surfactants is added to the electrolyte formulation in an amount sufficient to effect wettability of the separator membrane.

Discrete separators may be integrated into the laminar microbattery by direct placement into a designed cavity, pocket, or structure within the assembly. Desirably, this pocket may be formed by a spacer having a cutout that may be a geometric offset of the separator shape. Furthermore, the pocket may have a ledge or step on which the separator rests during assembly. The ledge or step may optionally include a pressure-sensitive adhesive which retains the discrete separator. Advantageously, the pressure-sensitive adhesive may be the same one used in the construction and stack up of other elements of an exemplary laminar microbattery.

Pressure Sensitive Adhesive

In some examples, the plurality of components comprising the laminar microbatteries of the present invention may be held together with a pressure-sensitive adhesive (PSA) that also serves as a sealant. While a myriad of commercially available pressure-sensitive adhesive formulations may exist, such formulations almost always include components that may make them unsuitable for use within a biocompatible laminar microbattery. Examples of undesirable components in pressure-sensitive adhesives may include low molecular mass leachable components, antioxidants e.g. BHT and/or MEHQ, plasticizing oils, impurities, oxidatively unstable moieties containing for example unsaturated chemical bonds, residual solvents and/or monomers, polymerization initiator fragments, polar tackifiers, and the like.

Suitable PSAs may on the other hand exhibit the following properties. They may be able to be applied to laminar components to achieve thin layers on the order of 2 to 20 microns. As well, they may contain a minimum of, for example, zero undesirable or non-biocompatible components. Additionally, they may have sufficient adhesive and cohesive properties so as to bind the components of the laminar battery together. And, they may be able to flow into the micron-scale features inherent in devices of the present construction while providing for a robust sealing of electrolyte within the battery. In some examples of suitable PSAs, the PSAs may have a low permeability to water vapor in order to maintain a desirable aqueous electrolyte composition within the battery even when the battery may be subjected to extremes in humidity for extended periods of time. The PSAs may have good chemical resistance to components of electrolytes such as acids, surfactants, and salts. They may be inert to the effects of water immersion. Suitable PSAs may have a low permeability to oxygen to minimize the rate of direct oxidation, which may be a form of self-discharge, of zinc anodes. And, they may facilitate a finite permeability to hydrogen gas, which may be slowly evolved from zinc anodes in aqueous electrolytes. This property of finite permeability to hydrogen gas may avoid a build-up of internal pressure.

In consideration of these requirements, polyisobutylene (PIB) may be a commercially-available material that may be formulated into PSA compositions meeting many if not all desirable requirements. Furthermore, PIB may be an excellent barrier sealant with very low water absorbance and low oxygen permeability. An example of PIB useful in the examples of the present invention may be Oppanol® B15 by BASF Corporation. Oppanol® B15 may be dissolved in hydrocarbon solvents such as toluene, dodecane, mineral spirits, and the like. One exemplary PSA composition may include 30 percent Oppanol® B15 (w/w) in a solvent mixture including 70 percent (w/w) toluene and 30 percent dodecane. The adhesive and rheological properties of PIB based PSA's may be determined in some examples by the blending of different molecular mass grades of PIB. A common approach may be to use a majority of low molar mass PIB, e.g. Oppanol® B10 to effect wetting, tack, and adhesion, and to use a minority of high molar mass PIB to effect toughness and resistance to flow. Consequently, blends of any number of PIB molar mass grades may be envisioned and may be practiced within the scope of the present invention. Furthermore, tackifiers may be added to the PSA formulation so long as the aforementioned requirements may be met. By their very nature, tackifiers impart polar properties to PSA formulations, so they may need to be used with caution so as to not adversely affect the barrier properties of the PSA. Furthermore, tackifiers may in some cases be oxidatively unstable and may include an antioxidant, which could leach out of the PSA. For these reasons, exemplary tackifiers for use in PSA's for biocompatible laminar microbatteries may include fully- or mostly hydrogenated hydrocarbon resin tackifiers such as the Regalrez series of tackifiers from Eastman Chemical Corporation.

Additional Package and Substrate Considerations in Biocompatible Battery Modules There may be numerous packaging and substrate considerations that may dictate desirable characteristics for package designs used in biocompatible laminar microbatteries. For example, the packaging may desirably be predominantly foil and/or film based where these packaging layers may be as thin as possible, for example, 10 to 50 microns. Additionally, the packaging may provide a sufficient diffusion barrier to moisture gain or loss during the shelf life. In many desirable examples, the packaging may provide a sufficient diffusion barrier to oxygen ingress to limit degradation of zinc anodes by direct oxidation.

In some examples, the packaging may provide a finite permeation pathway to hydrogen gas that may evolve due to direct reduction of water by zinc. And, the packaging may desirably sufficiently contain and may isolate the contents of the battery such that potential exposure to a user may be minimized.

In the present invention, packaging constructs may include the following types of functional components: namely, top and bottom packaging layers, PSA layers, spacer layers, interconnect zones, filling ports, and secondary packaging.

In some examples, top and bottom packaging layers may comprise metallic foils or polymer films. Top and bottom packaging layers may include multi-layer film constructs containing a plurality of polymer and/or barrier layers. Such film constructs may be referred to as coextruded barrier laminate films. An example of a commercial coextruded barrier laminate film of particular utility in the present invention may be 3M® Scotchpak 1109 backing which consists of a PET carrier web, a vapor-deposited aluminum barrier layer, and a polyethylene layer comprising a total average film thickness of 33 microns. Numerous other similar multilayer barrier films may be available and may be used in alternate examples of the present invention.

In design constructions comprising a PSA, packaging layer surface roughness may be of particular importance, because the PSA may also need to seal opposing packaging layer faces. Surface roughness may result from manufacturing processes used in foil and film production, for example, processes employing rolling, extruding, embossing and/or calendaring, among others. If the surface is too rough, PSA may not be able to be applied in a uniform thickness when the desired PSA thickness may be on the order of the surface roughness Ra. Furthermore, PSA's may not adequately seal against an opposing face if the opposing face has roughness that may be on the order of the PSA layer thickness. In the present invention, packaging materials having a surface roughness, Ra, less than 10 microns may be acceptable examples. In some examples, surface roughness values may be 5 microns or less. And, in still further examples, the surface roughness may be 1 micron or less. Surface roughness values may be measured by a variety of methods including but not limited to measurement techniques such as white light interferometry, stylus profilometry, and the like. There may be many examples in the art of surface metrology that surface roughness may be described by a number of alternative parameters and that the average surface roughness, Ra, values discussed herein may be meant to be representative of the types of features inherent in the aforementioned manufacturing processes.

Current Collectors and Electrodes

In some examples of zinc-carbon and Leclanché cells, the cathode current collector may be a sintered carbon rod. This type of material may face technical hurdles for thin electrochemical cells of the present invention. In some examples, printed carbon inks may be used in thin electrochemical cells to replace a sintered carbon rod for the cathode current collector, and in these examples, the resulting device may be formed without significant impairment to the resulting electrochemical cell. Typically, the carbon inks may be applied directly to packaging materials which may include polymer films, or in some cases metal foils. In the examples where the packaging film may be a metal foil, the carbon ink may need to protect the underlying metal foil from chemical degradation and/or corrosion by the electrolyte. Furthermore, in these examples, the carbon ink current collector may need to provide electrical conductivity from the inside of the electrochemical cell to the outside of the electrochemical cell, implying sealing around or through the carbon ink. Due to the porous nature of carbon inks, this may be not easily accomplished without significant challenges. Carbon inks also may be applied in layers that have finite and relatively small thickness, for example, 10 to 20 microns. In a thin electrochemical cell design in which the total internal package thickness may only be about 100 to 150 microns, the thickness of a carbon ink layer may take up a significant fraction of the total internal volume of the electrochemical cell, thereby negatively impacting electrical performance of the cell. Further, the thin nature of the overall battery and the current collector in particular may imply a small cross-sectional area for the current collector. As resistance of a trace increases with trace length and decreases with cross-sectional already, there may be a direct tradeoff between current collector thickness and resistance. The bulk resistivity of carbon ink may be insufficient to meet the resistance requirement of thin batteries. Inks filled with silver or other conductive metals may also be considered to decrease resistance and/or thickness, but they may introduce new challenges such as incompatibility with novel electrolytes. In consideration of these factors, in some examples it may be desirable to realize efficient and high performance thin electrochemical cells of the present invention by utilizing a thin metal foil as the current collector, or to apply a thin metal film to an underlying polymer packaging layer to act as the current collector. Such metal foils may have significantly lower resistivity, thereby allowing them to meet electrical resistance requirements with much less thickness than printed carbon inks.

In some examples, one or more of the top and/or bottom packaging layers may serve as a substrate for a sputtered current collector metal or metal stack. For example, 3M®

Scotchpak 1109 backing may be metallized using physical vapor deposition (PVD) of one or more metallic layers useful as a current collector for a cathode. Exemplary metal stacks useful as cathode current collectors may be Ti—W (Titanium-Tungsten) adhesion layers and Ti (Titanium) conductor layers. Exemplary metal stacks useful as anode current collectors may be Ti—W adhesion layers, Au (Gold) conductor layers, and In (Indium) deposition layers. The thickness of the PVD layers may, for example, be less than 500 nm in total. If multiple layers of metals are used, the electrochemical and barrier properties may need to be compatible with the battery. For example, copper may be electroplated on top of a seed layer to grow a thick layer of conductor. Additional layers may be plated upon the copper. However, copper may be electrochemically incompatible with certain electrolytes especially in the presence of zinc. Accordingly, if copper is used as a layer in the battery, it may need to be sufficiently isolated from the battery electrolyte. Alternatively, copper may be excluded or another metal substituted.

In some other examples, top and/or bottom packaging foils may also function as current collectors. For example, a 25 micron brass foil may be useful as an anode current collector for a zinc anode. The brass foil may be optionally electroplated with indium prior to electroplating with zinc. In one example, cathode current collector packaging foils may include titanium foil, Hastelloy C-276 foil, chromium foil, and/or tantalum foil. In certain designs, one or more packaging foils may be fine blanked, embossed, etched, textured, laser machined, or otherwise processed to provide desirable form, surface roughness, and/or geometry to the final cell packaging.

Anode and Anode Corrosion Inhibitors

The anode for the laminar battery of the present invention may, for example, comprise zinc. In traditional zinc carbon batteries, a zinc anode may take the physical form of a can in which the contents of the electrochemical cell may be contained. For the battery of the present invention, a zinc can may be an example but there may be other physical forms of zinc that may provide desirable to realize ultra-small battery designs.

Electroplated zinc may have examples of use in a number of industries, for example, for the protective or aesthetic coating of metal parts. In some examples, electroplated zinc may be used to form thin and conformal anodes useful for batteries of the present invention. Furthermore, the electroplated zinc may be patterned in seemingly endless configurations, depending on the design intent. A facile means for patterning electroplated zinc may be processing with the use of a photomask or a physical mask. A plating mask may be fabricated by a variety of approaches. One approach may be by using a photomask. In these examples, a photoresist may be applied to a conductive substrate, the substrate on which zinc may subsequently be plated. The desired plating pattern may be then projected to the photoresist by means of a photomask, thereby causing curing of selected areas of photoresist. The uncured photoresist may then be removed with appropriate solvent and cleaning techniques. The result may be a patterned area of conductive material that may receive an electroplated zinc treatment. While this method may provide benefit to the shape or design of the zinc to be plated, the approach may require use of available photopatternable materials, which may have constrained properties to the overall cell package construction. Consequently, new and novel methods for patterning zinc may be required to realize some designs of thin microbatteries of the present invention.

An alternative means of patterning zinc anodes may be by means of a physical mask application. A physical mask may be made by cutting desirable apertures in a film having desirable barrier and/or packaging properties. Additionally, the film may have pressure-sensitive adhesive applied to one or both sides. Finally, the film may have protective release liners applied to one or both adhesives. The release liner may serve the dual purpose of protecting the adhesive during aperture cutting and protecting the adhesive during specific processing steps of assembling the electrochemical cell, specifically the cathode filling step, described in following description. In some examples, a zinc mask may include a PET film of approximately 100 microns thickness to which a pressure-sensitive adhesive may be applied to both sides in a layer thickness of approximately 10-20 microns. Both PSA layers may be covered by a PET release film which may have a low surface energy surface treatment, and may have an approximate thickness of 50 microns. In these examples, the multi-layer zinc mask may comprise PSA and PET film. PET films and PET/PSA zinc mask constructs as described herein may be desirably processed with precision nanosecond laser micromachining equipment, such as an Oxford Lasers E-Series laser micromachining workstation, to create ultra-precise apertures in the mask to facilitate later plating. In essence, once the zinc mask has been fabricated, one side of the release liner may be removed, and the mask with apertures may be laminated to the anode current collector and/or anode-side packaging film/foil. In this manner, the PSA creates a seal at the inside edges of the apertures, facilitating clean and precise masking of the zinc during electroplating.

The zinc mask may be placed and then electroplating of one or more metallic materials may be performed. In some examples, zinc may be electroplated directly onto an electrochemically compatible anode current collector foil such as brass. In alternate design examples where the anode side packaging includes a polymer film or multi-layer polymer film upon which seed metallization has been applied, zinc, and/or the plating solutions used for depositing zinc, may not be chemically compatible with the underlying seed metallization. Manifestations of lack of compatibility may include film cracking, corrosion, and/or exacerbated $H_2$ evolution upon contact with cell electrolyte. In such a case, additional metals may be applied to the seed metal to affect better overall chemical compatibility in the system. One metal that may find particular utility in electrochemical cell constructions may be indium. Indium may be widely used as an alloying agent in battery grade zinc with its primary function being to provide an anti-corrosion property to the zinc in the presence of electrolyte. In some examples, indium may be successfully deposited on various seed metallizations such as Ti—W and Au. Resulting films of 1-3 microns of indium on the seed metallization layers may be low-stress and adherent. In this manner, the anode-side packaging film and attached current collector having an indium top layer may be conformable and durable. In some examples, it may be possible to deposit zinc on an indium-treated surface, the resulting deposit may be very non-uniform and nodular. This effect may occur at lower current density settings, for example 20 amps per square foot (ASF). As viewed under a microscope, nodules of zinc may be observed to form on the underlying smooth indium deposit. In certain electrochemical cell designs, the vertical space allowance for the zinc anode layer may be up to about 5-10 microns maximum, but in some examples, lower current densities may be used for zinc plating, and the resulting nodular growths may grow taller than the maximum anode vertical allowance. It may be that the nodular zinc growth stems from a combination of the high overpotential of indium and the presence of an oxide layer of indium.

In some examples, higher current density DC plating may overcome the relatively large nodular growth patterns of zinc on indium surfaces. For example, 100 ASF plating conditions may result in nodular zinc, but the size of the zinc nodules may be drastically reduced compared to 20 ASF plating conditions. Furthermore, the number of nodules may be vastly greater under 100 ASF plating conditions. The resulting zinc film may ultimately coalesce to a more or less uniform layer with only some residual feature of nodular growth while meeting the vertical space allowance of about 5-10 microns.

An added benefit of indium in the electrochemical cell may be reduction of hydrogen gas, which may be a slow process that occurs in aqueous electrochemical cells containing zinc. The indium may be beneficially applied to one or more of the anode current collector, the anode itself as a co-plated alloying component, or as a surface coating on the electroplated zinc. For the latter case, indium surface coatings may be desirably applied in situ by way of an electrolyte additive such as indium trichloride or indium acetate. When such additives may be added to the electrolyte in small concentrations, indium may spontaneously plate on exposed zinc surfaces as well as portions of exposed anode current collector.

Zinc, and similar anodes commonly used in commercial primary batteries, is typically found in sheet, rod, and paste forms. The anode of a miniature, biocompatible battery may be of similar form, e.g. thin foil, or may be plated as previously mentioned. The properties of this anode may differ significantly from those in existing batteries, for example, because of differences in contaminants or surface finish attributed to machining and plating processes. Accordingly, the electrodes and electrolyte may require special engineering to meet capacity, impedance, and shelf life requirements. For example, special plating process parameters, plating bath composition, surface treatment, and electrolyte composition may be needed to optimize electrode performance.

Cathode Mix

There may be numerous cathode chemistry mixes that may be consistent with the concepts of the present invention. In some examples, a cathode mix, which may be a term for a chemical formulation used to form a battery's cathode, may be applied as a paste or slurry and may include manganese dioxide, some form of conductive carbon such as carbon black or graphite, and other optional components. In some examples, these optional components may include one or more of binders, electrolyte salts, corrosion inhibitors, water or other solvents, surfactants, rheology modifiers, and other conductive additives such as conductive polymers. Once formulated and appropriately mixed, the cathode mix may have a desirable rheology that allows it to either be dispensed onto desired portions of the separator and/or cathode current collector, or squeegeed through a screen or stencil in a similar manner. In some examples, the cathode mix may be dried prior to later cell assembly steps, while in other examples, the cathode may contain some or all of the electrolyte components, and may only be partially dried to a selected moisture content.

The manganese dioxide which may be used in the cathode mix may, for example, be electrolytic manganese dioxide (EMD) due to the beneficial additional energy capacity that this type of manganese dioxide provides relative to other forms such as natural manganese dioxide or chemical manganese dioxide. Furthermore, the EMD useful in batteries of the present invention may need to have a particle size and particle size distribution that may be conductive to the formation of depositable or printable cathode mix pastes/slurries. Specifically, the EMD may be processed to remove significant large particulate components that would be considered large relative to other features such as battery internal dimensions, separator thicknesses, dispense tip diameters, stencil opening sizes, or screen mesh sizes. In some examples, EMD may have an average particle size of 7 microns with a large particle content that may contain particulates up to about 70 microns. In alternative examples, the EMD may be sieved, further milled, or otherwise separated or processed to limit large particulate content to below a certain threshold, for example, 25 microns or smaller. One process useful for the particle size reduction of EMD may be jet milling where sub-micron particulate may be obtained. Other processes useful for large particle size reduction may include ball milling or 3-roll milling of the cathode mix paste prior to use.

A critical aspect of the cathode mix paste may be the polymeric binder. The binder may serve a number of functions in the cathode mix paste. The primary function of the binder may be to create a sufficient inter-particle electrical network between EMD particles and carbon particles. A secondary function of the binder may be to facilitate electrical contact to the cathode current collector. A third function of the binder may be to influence the rheological properties of the cathode mix paste for advantageous dispensing and/or stenciling/screening. Still, a fourth function of the binder may be to enhance the electrolyte uptake and distribution within the cathode. The choice of the binder polymer as well as the specific amount to be used may be critical to the beneficial function of the cathode in the electrochemical cell of the present invention. If the binder polymer is too soluble in the electrolyte to be used, then the primary function of the binder, electrical continuity, may be drastically impacted to the point of cell non-functionality. On the contrary, if the binder polymer is insoluble in the electrolyte to be used, portions of EMD may be ionically insulated from the electrolyte, resulting in diminished cell performance such as reduced capacity, lower open circuit voltage, and/or increased internal resistance. In the end, choice of binder polymer and amount to be used may be a careful balancing act that may need to be determined by careful experimentation, in some examples using the design of experiments (DOE) approach. Examples of binder polymers useful for the present invention include polyvinylpyrrolidone, polyisobutylene, rubbery triblock copolymers including styrene end blocks such as those manufactured by Kraton Polymers, styrene-butadiene latex block copolymers, polyacrylic acid, hydroxyethylcellulose, carboxymethylcellulose, among others.

The cathode may also comprise silver dioxide or nickel oxyhydroxide among other candidate materials. Such materials may offer increased capacity and less decrease in loaded voltage during discharge relative to manganese dioxide, both desirable properties in a battery. Batteries based on these cathodes may have current examples present in industry and literature. A novel microbattery utilizing a silver dioxide cathode may include a biocompatible electrolyte, for example one including zinc chloride and/or ammonium chloride instead of potassium hydroxide.

Battery Architecture and Fabrication

Battery architecture and fabrication technology may be closely intertwined. As has been discussed in earlier sections of the present disclosure, a battery has the following elements: cathode, anode, separator, electrolyte, cathode current collector, anode current collector, and packaging. Clever design may try to combine these elements in easy to fabricate subassemblies. In other examples, optimized design may have dual-use components, such as using a metal package to double as a current collector. From a relative volume and thickness standpoint, these elements may be nearly all the same volume, except for the cathode. In some examples, the electrochemical system may require about two (2) to ten (10) times the volume of cathode as anode due to significant differences in mechanical density, energy density, discharge efficiency, material purity, and the presence of binders, fillers, and conductive agents. In these examples, the relative scale of the various components may be approximated in the following thicknesses of the elements: Anode current collector=1 µm; Cathode current collector=1 µm; Electrolyte=interstitial liquid (effectively 0 µm); Separator=as thin or thick as desired where the planned maximal thickness may be about 15 µm; Anode=5 µm; and the Cathode=50 µm. For these examples of elements the packaging needed to provide sufficient protection to maintain battery chemistry in use environments may have a planned maximal thickness of about 50 µm.

In some examples, which may be fundamentally different from large, prismatic constructs such as cylindrical or rectangular forms and which may be different than wafer-based solid state construct, such examples may assume a "pouch"-like construct, using webs or sheets fabricated into various configurations, with battery elements arranged inside. The containment may have two films or one film bent over onto the other side, either configuration of which may form two roughly planar surfaces, which may be then sealed on the perimeter to form a container. This thin-but-wide form factor may make battery elements themselves thin and wide. Furthermore, these examples may be suitable for application through coating, gravure printing, screen printing, sputtering, or other similar fabrication technology.

There may be numerous arrangements of the internal components, such as the anode, separator and cathode, in these "pouch-like" battery examples with thin-but-wide form factor. Within the enclosed region formed by the two films, these basic elements may be either "co-planar" that is side-by-side on the same plane or "co-facial" which may be face-to-face on opposite planes. In the co-planar arrangement, the anode, separator, and cathode may be deposited on the same surface. For the co-facial arrangement, the anode may be deposited on surface-1, the cathode may be deposited on surface-2, and the separator may be placed between the two, either deposited on one of the sides, or inserted as its own separate element.

Another type of example may be classified as laminate assembly, which may involve using films, either in a web or sheet form, to build up a battery layer by layer. Sheets may be bonded to each other using adhesives, such as pressure-sensitive adhesives, thermally activated adhesives, or chemical reaction-based adhesives. In some examples the sheets may be bonded by welding techniques such as thermal welding, ultrasonic welding and the like. Sheets may lend themselves to standard industry practices as roll-to-roll (R2R), or sheet-to-sheet assembly. As indicted earlier, an interior volume for cathode may need to be substantially larger than the other active elements in the battery. Much of a battery construct may have to create the space of this cathode material, and support it from migration during flexing of the battery. Another portion of the battery construct that may consume significant portions of the thickness budget may be the separator material. In some examples, a sheet form of separator may create an advantageous solution for laminate processing. In other examples, the separator may be formed by dispensing hydrogel material into a layer to act as the separator.

In these laminate battery assembly examples, the forming product may have an anode sheet, which may be a combination of a package layer and an anode current collector, as well as substrate for the anode layer. The forming product may also have an optional separator spacer sheet, a cathode spacer sheet, and a cathode sheet. The cathode sheet may be a combination of a package layer and a cathode current collector layer.

Intimate contact between electrodes and current collectors is of critical importance for reducing impedance and increasing discharge capacity. If portions of the electrode are not in contact with the current collector, resistance may increase since conductivity is then through the electrode (typically less conductive than the current collector) or a portion of the electrode may become totally disconnected. In coin cell and cylindrical batteries, intimacy is realized with mechanical force to crimp the can, pack paste into a can, or through similar means. Wave washers or similar springs are used in commercial cells to maintain force within the battery; however, these would add to the overall thickness of a miniature battery. In typical patch batteries, a separator may be saturated in electrolyte, placed across the electrodes, and pressed down by the external packaging. In a laminar, cofacial battery there are several methods to increase electrode intimacy. The anode may be plated directly onto the current collector rather than using a paste. This process inherently results in a high level of intimacy and conductivity. The cathode, however, is typically a paste. Although binder material present in the cathode paste may provide adhesion and cohesion, mechanical pressure may be needed to ensure the cathode paste remains in contact with the cathode current collector. This may be especially important as the package is flexed and the battery ages and discharges, for example, as moisture leaves the package through thin and small seals. Compression of the cathode may be achieved in the laminar, cofacial battery by introducing a compliant separator and/or electrolyte between the anode and cathode. A gel electrolyte or hydrogel separator, for example, may compress on assembly and not simply run out of the battery as a liquid electrolyte would. Once the battery is sealed, the electrolyte and/or separator may then push back against the cathode. An embossing step may be performed after assembly of the laminar stack, introducing compression into the stack.

Figures 4M, 4N:
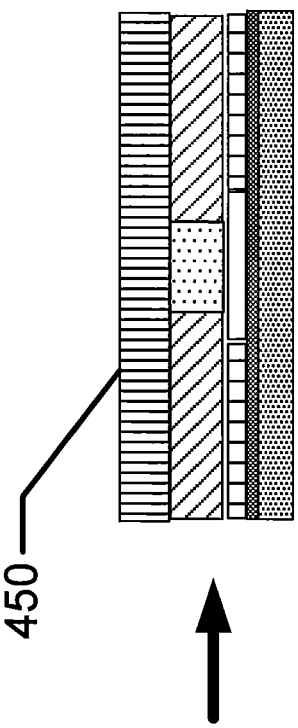

Exemplary Illustrated Processing of Biocompatible Energization Elements—Placed Separator An example of the steps that may be involved in processing biocompatible energization elements may be found referring to FIGS. 4A-4N. The processing at some of the exemplary steps may be found in the individual figures. In FIG. 4A, a combination of a PET Cathode Spacer 401 and a PET Gap Spacer 404 may be illustrated. The PET Cathode Spacer 401 may be formed by applying films of PET 403 which, for example, may be roughly 3 mils thick. On either side of the PET layer may be found PSA layers or these may be capped with a polyvinylidene fluoride (PVDF) release layer 402 which may be roughly 1 mil in thickness. The PET Gap spacer 404 may be formed of a PVDF layer 409 which may be roughly 3 mils in thickness. There may be a capping PET layer 405 which may be roughly 0.5 mils in thickness. Between the PVDF layer 409 and the capping PET layer 405, in some examples, may be a layer of PSA.

Proceeding to FIG. 4B, a cavity 406 in the Gap spacer layer may be cut by laser cutting treatment. Next at FIG. 4C, the cut PET Gap spacer layer may be laminated 408 to the PET Cathode Spacer layer. Proceeding to FIG. 4D, a cathode spacer cavity 410 may be cut by laser cutting treatment. The alignment of this cutting step may be registered to the previously cut features in the PET Gap spacer Layer. At FIG. 4E, a layer of Celgard 412, for an ultimate separator layer, may be bonded to a carrier 411. Proceeding to FIG. 4F, the Celgard material may be cut to figures that are between the size of the previous two laser cut cavities, and approximately the size of the PET gap spacer cavity, forming a precut separator 420. Proceeding to FIG. 4G, a pick and place tool 421 may be used to pick and place discrete pieces of Celgard into their desired locations on the growing device. At FIG. 4H, the placed Celgard pieces 422 are fastened into place and then the PVDF release layer 423 may be removed. Proceeding to FIG. 4I, the growing device structure may be bonded to a film of the anode 425. The anode may comprise an anode collector film upon which a zinc anode film has been electrodeposited.

Proceeding to FIG. 4J, a cathode slurry 430 may be placed into the formed gap. A squeegee 431 may be used in some examples to spread the cathode mix across a work piece and in the process fill the gaps of the battery devices being formed. After filling, the remaining PVDF release layer 432 may be removed which may result in the structure illustrated in FIG. 4K. At FIG. 4L the entire structure may be subjected to a drying process which may shrink the cathode slurry 440 to also be at the height of the PET layer top. Proceeding to FIG. 4M, a cathode film layer 450, which may already have the cathode collector film upon it, may be bonded to the growing structure. In a final illustration at FIG. 4N a laser cutting process may be performed to remove side regions 460 and yield a battery element 470. There may be numerous alterations, deletions, changes to materials and thickness targets that may be useful within the intent of the present invention.

Figure 5:
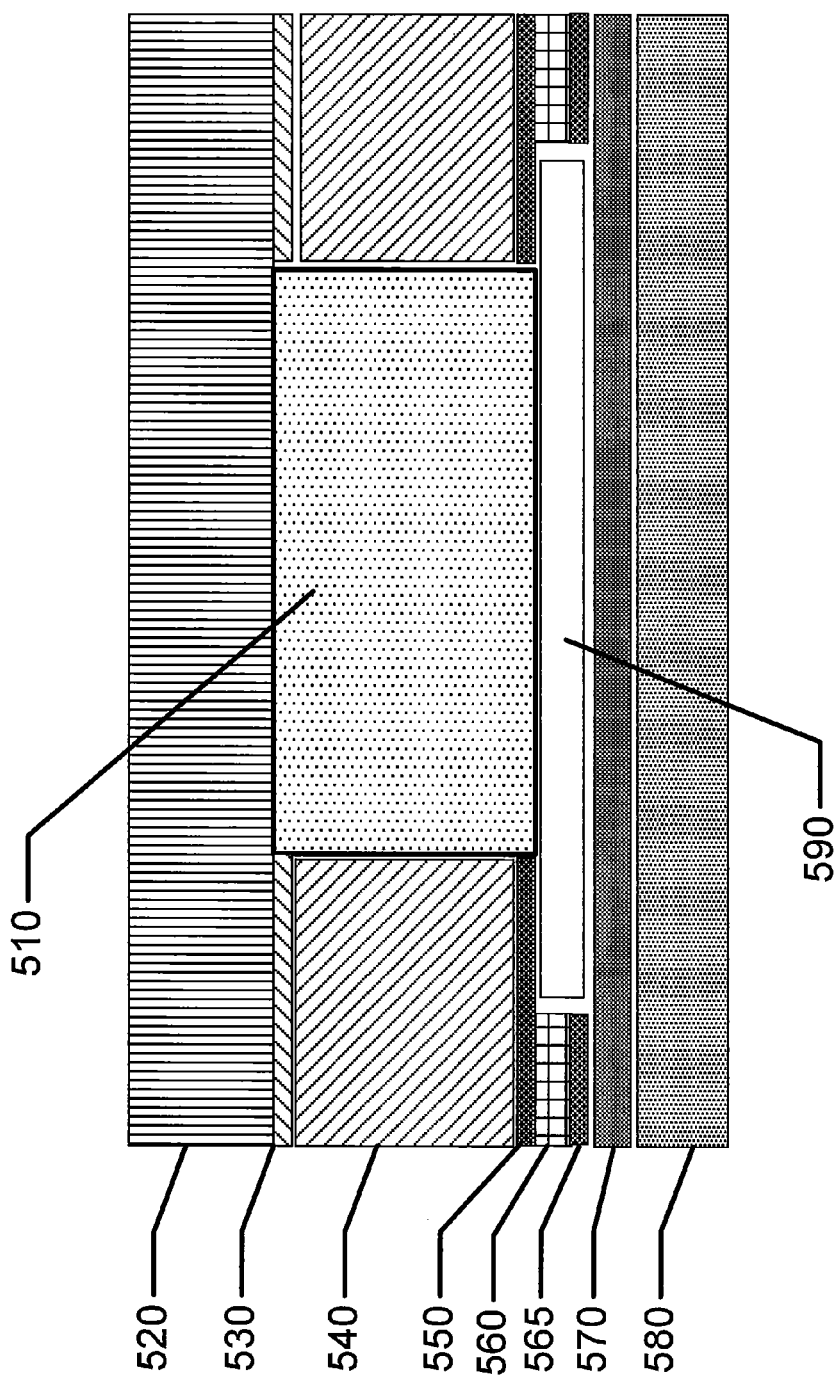
FIG. 5 illustrates an exemplary fully formed biocompatible energization element.

The result of the exemplary processing may be depicted in some detail at FIG. 5. In an example, the following reference features may be defined. The Cathode chemistry 510 may be located in contact with the cathode and cathode collector 520. A pressure-sensitive adhesive layer 530 may hold and seal the cathode collector 520 to a PET Spacer layer 540. On the other side of the PET Spacer layer 540, may be another PSA layer 550, which seals and adheres the PET Spacer layer 540 to the PET Gap layer 560. Another PSA layer 565 may seal and adhere the PET Gap layer 560 to the Anode and Anode Current Collector layers. A Zinc Plated layer 570 may be plated onto the Anode Current Collector 580. The separator layer 590 may be located within the structure to perform the associated functions as have been defined in the present invention. In some examples, an electrolyte may be added during the processing of the device, in other examples, the separator may already include electrolyte.

Exemplary Processing Illustration of Biocompatible Energization Elements—Deposited Separator An example of the steps that may be involved in processing biocompatible energization elements may be found in FIGS. 6A-6F. The processing at some of the exemplary steps may be found in the individual figures. There may be numerous alterations, deletions, changes to materials and thickness targets that may be useful within the intent of the present invention.

In FIG. 6A, a laminar construct 600 may be illustrated. The laminar structure may comprise two laminar construct release layers, 602 and 602a; two laminar construct adhesive layers 604 and 604a, located between the laminar construct release layers 602 and 602a; and a laminar construct core 606, located between the two laminar construct adhesive layers 604 and 604a. The laminar construct release layers, 602 and 602a, and adhesive layers, 604 and 604a, may be produced or purchased, such as a commercially available pressure-sensitive adhesive transfer tape with primary liner layer. The laminar construct adhesive layers may be a PVDF layer which may be approximately 1-3 millimeters in thickness and cap the laminar construct core 606. The laminar construct core 606 may comprise a thermoplastic polymer resin such as polyethylene terephthalate, which for example may be roughly 3 millimeters thick. Proceeding to FIG. 6B, a cavity for the cathode pocket 608 may be cut in the laminar construct by laser cutting treatment.

Next, at FIG. 6C, the bottom laminar construct release layer 602a may be removed from the laminar construct, exposing the laminar construct adhesive layer 604a. The laminar construct adhesive layer 604a may then be used to adhere an anode connection foil 610 to cover the bottom opening of the cathode pocket 608. Proceeding to FIG. 6D, the anode connection foil 610 may be protected on the exposed bottom layer by adhering a masking layer 612. The masking layer 612 may be a commercially available PSA transfer tape with a primary liner. Next, at FIG. 6E, the anode connection foil 610 may be electroplated with a coherent metal 614, zinc for example, which coats the exposed section of the anode connection foil 610 inside of the cathode pocket. Proceeding to 6F, the anode electrical collection masking layer 612 is removed from the bottom of the anode connection foil 610 after electroplating.

FIGS. 7A-7F may illustrate an alternate mode of processing the method steps illustrated in FIGS. 6A-6F. FIGS. 7A-7B may illustrate similar processes as depicted in FIGS. 6A-6B. The laminar structure may comprise two laminar construct release layers, 702 and 702a, one layer on either end; two laminar construct adhesive layers, 704 and 704a, located between the laminar construct release layers 702 and 702a; and a laminar construct core 706, located between the two laminar construct adhesive layers 704 and 704a. The laminar construct release layers and adhesive layers may be produced or purchased, such as a commercially available pressure-sensitive adhesive transfer tape with primary liner layer. The laminar construct adhesive layers may be a polyvinylidene fluoride (PVDF) layer which may be approximately 1-3 millimeters in thickness and cap the laminar construct core 706. The laminar construct core 706 may comprise a thermoplastic polymer resin such as polyethylene terephthalate, which for example may be roughly 3 millimeters thick. Proceeding to FIG. 7B, a cavity for the cathode pocket 708 may be cut in the laminar construct by laser cutting treatment. In FIG. 7C, an anode connection foil 710 may be obtained and a protective masking layer 712 applied to one side. Next, at FIG. 7D, the anode connection foil 710 may be electroplated with a layer 714 of a coherent metal, for example, zinc. Proceeding to FIG. 7E, the laminar constructs of FIGS. 7B and 7D may be combined to form a new laminar construct as depicted in FIG. 7E by adhering FIG. 7B to the electroplated layer 714 of FIG. 7D. The release layer 702a of FIG. 7B may be removed in order to expose adhesive layer 704a of FIG. 7B for adherence onto electroplated layer 714 of FIG. 7D. Proceeding next to FIG. 7F, the anode protective masking layer 712 may be removed from the bottom of the anode connection foil 710.

FIGS. 8A-8H may illustrate implementation of energization elements to a biocompatible laminar structure, which at times is referred to as a laminar assembly or a laminate assembly herein, similar to, for example, those illustrated in FIGS. 6A-6F and 7A-7F. Proceeding to FIG. 8A, a hydrogel separator precursor mixture 820 may be deposited on the surface of the laminate assembly. In some examples, as depicted, the hydrogel precursor mixture 820 may be applied upon a release layer 802. Next, at FIG. 8B, the hydrogel separator precursor mixture 820 may be squeegeed 850 into the cathode pocket while being cleaned off of the release layer 802. The term "squeegeed" may generally refer to the use of a planarizing or scraping tool to rub across the surface and move fluid material over the surface and into cavities as they exist. The process of squeegeeing may be performed by equipment similar to the vernacular "Squeegee" type device or alternatively and planarizing device such as knife edges, razor edges and the like which may be made of numerous materials as may be chemically consistent with the material to be moved.

The processing depicted at FIG. 8B may be performed several times to ensure coating of the cathode pocket, and increment the thickness of resulting features. Next, at FIG. 8C, the hydrogel separator precursor mixture may be allowed to dry in order to evaporate materials, which may typically be solvents or diluents of various types, from the hydrogel separator precursor mixture; then, the dispensed and applied materials may be cured. It may be possible to repeat both of the processes depicted at FIG. 8B and FIG. 8C in combination in some examples. In some examples, the hydrogel separator precursor mixture may be cured by exposure to heat while in other examples the curing may be performed by exposure to photon energy. In still further examples the curing may involve both exposure to photon energy and to heat. There may be numerous manners to cure the hydrogel separator precursor mixture.

The result of curing may be to form the hydrogel separator precursor material to the wall of the cathode pocket as well as the surface region in proximity to an anode or cathode feature which in the present example may be an anode feature. Adherence of the material to the sidewalls of the cavity may be useful in the separation function of a separator. The result of curing may be to form a dehydrated polymerized precursor mixture concentrate 822 which may be simply considered the separator of the cell. Proceeding to FIG. 8D, cathode slurry 830 may be deposited onto the surface of the laminar construct release layer 802. Next, at FIG. 8E the cathode slurry 830 may be squeegeed into the cathode pocket and onto the dehydrated polymerized precursor mixture concentrate 822. The cathode slurry may be moved to its desired location in the cavity while simultaneously being cleaned off to a large degree from the laminar construct release layer 802. The process of FIG. 8E may be performed several times to ensure coating of the cathode slurry 830 on top of the dehydrated polymerized precursor mixture concentrate 822. Next, at FIG. 8F, the cathode slurry may be allowed to dry down to form an isolated cathode fill 832 on top of the dehydrated polymerized precursor mixture concentrate 822, filling in the remainder of the cathode pocket.

Proceeding to FIG. 8G, an electrolyte formulation 840 may be added on to the isolated cathode fill 832 and allowed to hydrate the isolated cathode fill 832 and the dehydrated polymerized precursor mixture concentrate 822. Next, at FIG. 8H, a cathode connection foil 816 may be adhered to the remaining laminar construct adhesive layer 804 by removing the remaining laminar construct release layer 802 and pressing the connection foil 816 in place. The resulting placement may result in covering the hydrated cathode fill 842 as well as establishing electrical contact to the cathode fill 842 as a cathode current collector and connection means.

FIGS. 9A through 9C may illustrate an alternative example of the resulting laminate assembly illustrated in FIG. 7D. In FIG. 9A, the anode connection foil 710 may be obtained and a protective masking layer 712 applied to one side. The anode connection foil 710 may be plated with a layer 714 of coherent metal with, for example, zinc in a similar fashion as described in the previous figures. Proceeding to FIG. 9B, a hydrogel separator 910 may be applied without the use of the squeegee method illustrated in FIG. 8E. The hydrogel separator precursor mixture may be applied in various manners, for example a preformed film of the mixture may be adhered by physical adherence, and alternatively a diluted mixture of the hydrogel separator precursor mixture may be dispensed and then adjusted to a desired thickness by the processing of spin coating. Alternatively the material may be applied by spray coating, or any other processing equivalent.

Next, at FIG. 9C, processing is depicted to create a segment of the hydrogel separator that may function as a containment around a separator region. The processing may create a region that limits the flow, or diffusion, of materials such as electrolyte outside the internal structure of the formed battery elements. Such a blocking feature 920 of various types may therefore be formed. The blocking feature, in some examples, may correspond to a highly cross-linked region of the separator layer as may be formed in some examples by increased exposure to photon energy in the desired region of the blocking feature 920. In other examples, materials may be added to the hydrogel separator material before it is cured to create regionally differentiated portions that upon curing become the blocking feature 920. In still further examples, regions of the hydrogel separator material may be removed either before or after curing by various techniques including for example chemical etch of the layer with masking to define the regional extent. The region of removed material may create a blocking feature in its own right or alternatively materially may be added back into the void to create a blocking feature. The processing of the impermeable segment may occur through several methods including but not limited to: image out processing, increased cross-linking, heavy photodosing, back-filling, or omission of hydrogel adherence to create a void. In some examples, a laminate construct or assembly of the type depicted as the result of the processing in FIG. 9C may be formed without the blocking feature 920.

Polymerized Battery Element Separators

In some battery designs, the use of a discrete separator (as described in a previous section) may be precluded due to a variety of reasons such as the cost, the availability of materials, the quality of materials, or the complexity of processing for some material options as non-limiting examples. In such cases, a cast or form-in-place separator which may have been depicted in the processes of FIGS. 8A-8H, for example, may provide desirable benefits. While starch or pasted separators have been used commercially with success in AA and other format Leclanche or zinc carbon batteries, such separators may be unsuitable in some ways for use in certain examples of laminar microbatteries. Particular attention may need to be paid to the uniformity and consistency of geometry for any separator used in the batteries of the present invention. Precise control over separator volume may be needed to facilitate precise subsequent incorporation of known cathode volumes and subsequent realization of consistent discharge capacities and cell performance.

A method to achieve a uniform, mechanically robust form-in-place separator may be to use UV-curable hydrogel formulations. Numerous water-permeable hydrogel formulations may be known in various industries, for example, the contact lens industry. An example of a common hydrogel in the contact lens industry may be poly (hydroxyethylmethacrylate) crosslinked gel, or simply pHEMA. For numerous applications of the present invention, pHEMA may possess many attractive properties for use in Leclanche and zinc carbon batteries. pHEMA typically may maintain a water content of approximately 30-40 percent in the hydrated state while maintaining an elastic modulus of about 100 psi or greater. Furthermore, the modulus and water content properties of crosslinked hydrogels may be adjusted by one of skill in the art by incorporating additional hydrophilic monomeric (e.g. methacrylic acid) or polymeric (e.g. polyvinylpyrrolidone) components. In this manner, the water content, or more specifically, the ionic permeability of the hydrogel may be adjusted by formulation.

Of particular advantage in some examples, a castable and polymerizable hydrogel formulation may contain one or more diluents to facilitate processing. The diluent may be chosen to be volatile such that the castable mixture may be squeegeed into a cavity, and then allowed a sufficient drying time to remove the volatile solvent component. After drying, a bulk photopolymerization may be initiated by exposure to actinic radiation of appropriate wavelength, such as blue UV light at 420 nm, for the chosen photoinitiator, such as CG 819. The volatile diluent may help to provide a desirable application viscosity so as to facilitate casting a uniform layer of polymerizable material in the cavity. The volatile diluent may also provide beneficial surface tension lowering effects, particularly in the case where strongly polar monomers are incorporated in the formulation. Another aspect that may be important to achieve the casting of a uniform layer of polymerizable material in the cavity may be the application viscosity. Common small molar mass reactive monomers typically do not have very high viscosities, which may be typically only a few centipoise. In an effort to provide beneficial viscosity control of the castable and polymerizable separator material, a high molar mass polymeric component known to be compatible with the polymerizable material may be selected for incorporation into the formulation. Examples of high molar mass polymers which may be suitable for incorporation into exemplary formulations may include polyvinylpyrrolidone and polyethylene oxide.

In some examples the castable, polymerizable separator may be advantageously applied into a designed cavity, as previously described. In alternative examples, there may be no cavity at the time of polymerization. Instead, the castable, polymerizable separator formulation may be coated onto an electrode-containing substrate, for example patterned zinc plated brass, and then subsequently exposed to actinic radiation using a photomask to selectively polymerize the separator material in targeted areas. Unreacted separator material may then be removed by exposure to appropriate rinsing solvents. In these examples, the separator material may be designated as a photo-patternable separator.

The biocompatible devices may be, for example, implantable electronic devices, such as pacemakers and micro-energy harvesters, electronic pills for monitoring and/or testing a biological function, surgical devices with active components, ophthalmic devices, microsized pumps, defibrillators, stents, and the like.

Specific examples have been described to illustrate sample embodiments for the formation, methods of formation, and apparatus of formation of biocompatible energization elements comprising separators. These examples are for the illustration and are not intended to limit the scope of the claims in any manner. Accordingly, the description is intended to embrace all examples that may be apparent to those skilled in the art.

What is claimed is:

1. A method of forming a biocompatible energization element, the method comprising:
   receiving a first substrate film of a first insulating material;
   cutting a cavity in the first substrate film to form a cathode spacer layer, wherein an edge of the cavity defines a sidewall of the cavity;
   receiving an anode film;
   adhering a first surface of the cathode spacer layer to a first surface of the anode film;
   depositing a separator into the cavity in the cathode spacer layer;
   receiving a cathode slurry; and
   placing the cathode slurry into the cavity in the cathode spacer layer, wherein the sidewall of the cavity in the cathode spacer layer and a surface of the deposited separator contain the cathode slurry.

2. The method of claim 1 further comprising:
   receiving a cathode contact film; and
   adhering a second surface of the cathode spacer layer to at least a portion of a first surface of the cathode contact film.

3. The method of claim 2 further comprising:
   receiving a first packaging film comprising a film stack wherein one layer is a metallic moisture barrier; and
   adhering the first packaging film to at least a portion of a second surface of the cathode contact film.

4. The method of claim 3 further comprising:
   receiving a second packaging film comprising a film stack wherein one film layer is a metallic moisture barrier; and
   adhering the second packaging film to at least a portion of a second surface of the anode film.

5. The method of claim 4 further comprising:
   adhering the biocompatible energization element to a portion of a biomedical device, wherein the cathode slurry is contained at least partially by the sidewall of the cavity in the cathode spacer layer, by the first packaging film and by the second packaging film.

6. The method of claim 2 wherein the biocompatible energization element is added to an insert of a biomedical device, wherein the biocompatible energization element is sealed within the insert, wherein the cathode slurry is contained at least partially by the sidewall of the cavity in the cathode spacer layer and by the insert.

7. The method of claim 6 wherein the biomedical device is a contact lens.

8. The method of claim 1 further comprising adding an electrolyte formulation upon the separator.

9. The method of claim 8 wherein the adding of the electrolyte formulation upon the separator is performed before the placing of the cathode slurry.

10. The method of claim 1 wherein the cathode slurry comprises manganese dioxide.

11. The method of claim 10 wherein the manganese dioxide comprises electrolytic manganese dioxide.

12. The method of claim 11 further comprising processing of the cathode slurry to remove large particulates.

13. The method of claim 12 wherein particle sizes are less than approximately 70 microns.

14. The method of claim 13 wherein the particle sizes are less than approximately 25 microns.

15. The method of claim 12 wherein the processing to remove large particulates comprises ball milling.

16. The method of claim 12 wherein the processing to remove large particulates comprises jet milling.

17. The method of claim 1 wherein the first substrate film is polyethylene terephthalate.

18. The method of claim 1 wherein the cutting of the cavity in the first substrate film utilizes a laser.

19. The method of claim 1 wherein the method of adhering comprises activating a pressure-sensitive adhesive.

20. The method of claim 1 wherein multiple cavities are cut into the cathode spacer layer, and the separator is deposited into at least two of the multiple cavities.

21. The method of claim 1 further comprising:
electroplating a zinc layer upon the anode film before adhering the first surface of the anode to the first surface of the cathode spacer layer, wherein the surface of the electroplated zinc layer subsequently becomes the first surface of the anode film.

22. The method of claim 1 the method further comprising:
electrically contacting the biocompatible energization element to an electronic circuit; and
electrically contacting the electronic circuit to an electroactive element of a biomedical device.

23. The method of claim 22 further comprising bending the device resulting from claim 22 to form a conical-shaped piece by joining two ends of the device resulting from claim 22.

24. A method of forming a biocompatible energization element, the method comprising:
receiving a first substrate film of a first insulating material;
cutting a cavity in the first substrate film to form a cathode spacer layer, wherein an edge of the cavity defines a sidewall of the cavity;
receiving an anode film;
depositing a separator onto a first surface of the anode film;
adhering a first surface of the cathode spacer layer to a first surface of the deposited separator;
receiving a cathode slurry; and
placing the cathode slurry into the cavity in the cathode spacer layer, wherein the sidewall of the cavity in the cathode spacer layer and the first surface of the deposited separator contain the cathode slurry.

25. The method of claim 24 further comprising:
receiving a cathode contact film; and
adhering a second surface of the cathode spacer layer to at least a portion of a first surface of the cathode contact film.

26. The method of claim 25 further comprising:
receiving a first packaging film comprising a film stack wherein one layer is a metallic moisture barrier; and
adhering the first packaging film to at least a portion of a second surface of the cathode contact film.

27. The method of claim 26 further comprising:
receiving a second packaging film comprising a film stack wherein one film layer is a metallic moisture barrier; and
adhering the second packaging film to at least a portion of a second surface of the anode film.

28. The method of claim 27 further comprising:
adhering the biocompatible energization element to a portion of a biomedical device, wherein the cathode slurry is contained at least partially by the sidewall of the cavity in the cathode spacer layer, by the first packaging film and by the second packaging film.

29. The method of claim 25 wherein the biocompatible energization element is added to an insert of a biomedical device, wherein the biocompatible energization element is sealed within the insert, wherein the cathode slurry is contained at least partially by the sidewall of the cavity in the cathode spacer layer and by the insert.

30. The method of claim 29 wherein the biomedical device is a contact lens.

* * * * *